US012605247B2

(12) United States Patent
Schwarcz et al.

(10) Patent No.: US 12,605,247 B2
(45) Date of Patent: Apr. 21, 2026

(54) HANDLE LOCKING MECHANISMS FOR A TRANSCATHETER DELIVERY SYSTEM

(71) Applicant: Edwards Lifesciences Corporation, Irvine, CA (US)

(72) Inventors: Elazar Levi Schwarcz, Netanya (IL); Ofir Witzman, Harish (IL); Oren Cohen, Kadima (IL)

(73) Assignee: Edwards Lifesciences Corporation, Irvine, CA (US)

( * ) Notice: Subject to any disclaimer, the term of this patent is extended or adjusted under 35 U.S.C. 154(b) by 818 days.

(21) Appl. No.: 17/860,330

(22) Filed: Jul. 8, 2022

(65) Prior Publication Data

US 2022/0338987 A1     Oct. 27, 2022

Related U.S. Application Data

(63) Continuation of application No. PCT/US2021/012156, filed on Jan. 5, 2021.

(60) Provisional application No. 62/960,516, filed on Jan. 13, 2020.

(51) Int. Cl.
     *A61F 2/24*      (2006.01)
     *A61F 2/95*      (2013.01)

(52) U.S. Cl.
     CPC .......... *A61F 2/2436* (2013.01); *A61F 2/2418* (2013.01); *A61F 2/95* (2013.01); *A61F 2250/0039* (2013.01)

(58) Field of Classification Search
     None
     See application file for complete search history.

(56) References Cited

U.S. PATENT DOCUMENTS

| | | | |
|---|---|---|---|
| 43,882 | A | 8/1864 | Marshall |
| 519,297 | A | 5/1894 | Wanek et al. |
| 4,035,849 | A | 7/1977 | Angell et al. |
| 4,592,340 | A | 6/1986 | Boyles |
| 4,665,918 | A * | 5/1987 | Garza ........................ A61F 2/95 623/1.11 |
| 4,955,895 | A | 9/1990 | Sugiyama et al. |
| 4,994,077 | A | 2/1991 | Dobben |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Shaun L David

(74) *Attorney, Agent, or Firm* — Klarquist Sparkman, LLP

(57)     ABSTRACT

A locking mechanism for a transcatheter delivery system is disclosed. As one example, the locking mechanism may comprise a first fixing member configured to be coupled to an introducer sheath, a second fixing member configured to be coupled to a handle of a delivery apparatus, and a locking arm configured to be removably coupled at a first end to one of the first fixing member and the second fixing member and fixedly or removably coupled at a second end to another one of the first fixing member and the second fixing member, wherein the locking arm is moveable between a first position where an axial position of the second fixing member is not fixed relative to the first fixing member via the locking arm and a second position where the axial position of the second fixing member is fixed relative to the first fixing member via the locking arm.

20 Claims, 7 Drawing Sheets

(56)                    References Cited

U.S. PATENT DOCUMENTS

| | | | |
|---|---|---|---|
| 5,059,177 A | 10/1991 | Towne et al. | |
| 5,176,698 A | 1/1993 | Burns et al. | |
| 5,192,297 A | 3/1993 | Hull | |
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,683,451 A * | 11/1997 | Lenker | A61F 2/91 |
| | | | 606/198 |
| 5,707,376 A * | 1/1998 | Kavteladze | A61F 2/90 |
| | | | 623/1.11 |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 | 10/2017 | Tran et al. | |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno Azizi | |
| 2006/0025857 A1 | 2/2006 | Bergheim et al. | |
| 2006/0282150 A1 | 12/2006 | Olson et al. | |
| 2007/0005131 A1 | 1/2007 | Taylor | |
| 2007/0050000 A1 * | 3/2007 | Esch | A61B 18/082 |
| | | | 607/113 |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 * | 9/2009 | Taylor | A61F 2/2439 |
| | | | 623/1.12 |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0028894 A1 * | 2/2011 | Foley | A61M 25/0136 |
| | | | 604/95.01 |
| 2011/0054596 A1 | 3/2011 | Taylor | |
| 2011/0105954 A1 * | 5/2011 | Cohen | A61B 5/6852 |
| | | | 604/95.04 |
| 2011/0137331 A1 | 6/2011 | Walsh et al. | |

(56)                    References Cited

U.S. PATENT DOCUMENTS

| | | | |
|---|---|---|---|
| 2011/0160846 A1 | 6/2011 | Bishop et al. | |
| 2011/0202053 A1* | 8/2011 | Moss | A61B 18/1477 |
| | | | 606/41 |
| 2012/0123529 A1 | 5/2012 | Levi et al. | |
| 2012/0226341 A1* | 9/2012 | Schreck | A61F 2/07 |
| | | | 623/1.11 |
| 2012/0239142 A1 | 9/2012 | Liu et al. | |
| 2013/0030519 A1 | 1/2013 | Tran et al. | |
| 2013/0317598 A1 | 11/2013 | Rowe et al. | |
| 2014/0296962 A1 | 10/2014 | Cartledge et al. | |
| 2017/0065415 A1 | 3/2017 | Rupp et al. | |
| 2018/0153689 A1 | 6/2018 | Maimon et al. | |
| 2018/0177516 A1* | 6/2018 | Vardi | A61B 34/73 |
| 2018/0344456 A1 | 12/2018 | Barash et al. | |
| 2020/0297489 A1* | 9/2020 | Bishop | A61B 17/0487 |
| 2020/0405485 A1* | 12/2020 | Rohl | A61F 2/2466 |
| 2022/0104800 A1* | 4/2022 | Kachaamy | A61B 18/082 |

FOREIGN PATENT DOCUMENTS

| | | | |
|---|---|---|---|
| EP | 0592410 B1 | 10/1995 | |
| EP | 0850607 A1 | 7/1998 | |
| EP | 3334382 A1 | 6/2018 | |
| FR | 2815844 A1 | 5/2002 | |
| WO | 1991017720 A1 | 11/1991 | |
| WO | 1998029057 A1 | 7/1998 | |
| WO | 1999012483 A1 | 3/1999 | |
| WO | 2001049213 A2 | 7/2001 | |
| WO | 2001054625 A1 | 8/2001 | |
| WO | 2001076510 A2 | 10/2001 | |
| WO | 2002022054 A1 | 3/2002 | |
| WO | 2002036048 A1 | 5/2002 | |
| WO | 2002047575 A2 | 6/2002 | |
| WO | 2002060352 A1 | 8/2002 | |
| WO | 2003030776 A2 | 4/2003 | |
| WO | 2003047468 A1 | 6/2003 | |
| WO | 2004019825 A1 | 3/2004 | |
| WO | 2005084595 A1 | 9/2005 | |
| WO | 2005102015 A2 | 11/2005 | |
| WO | 2006032051 A2 | 3/2006 | |
| WO | 2006111391 A1 | 10/2006 | |
| WO | 2006138173 A2 | 12/2006 | |
| WO | 2007047488 A2 | 4/2007 | |
| WO | 2007067942 A1 | 6/2007 | |
| WO | 2010121076 A2 | 10/2010 | |
| WO | WO-2019237003 A1 | 12/2019 | |

* cited by examiner

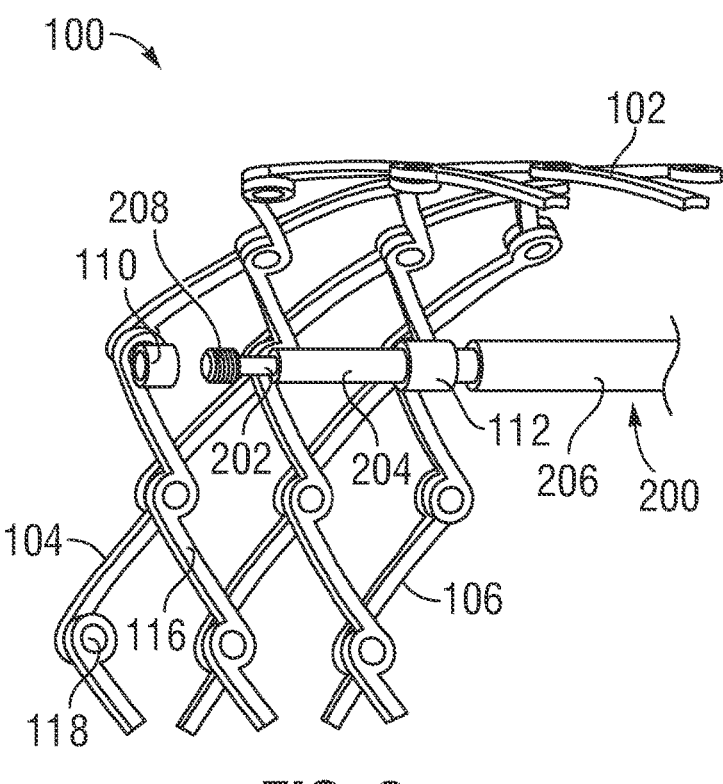
FIG. 2
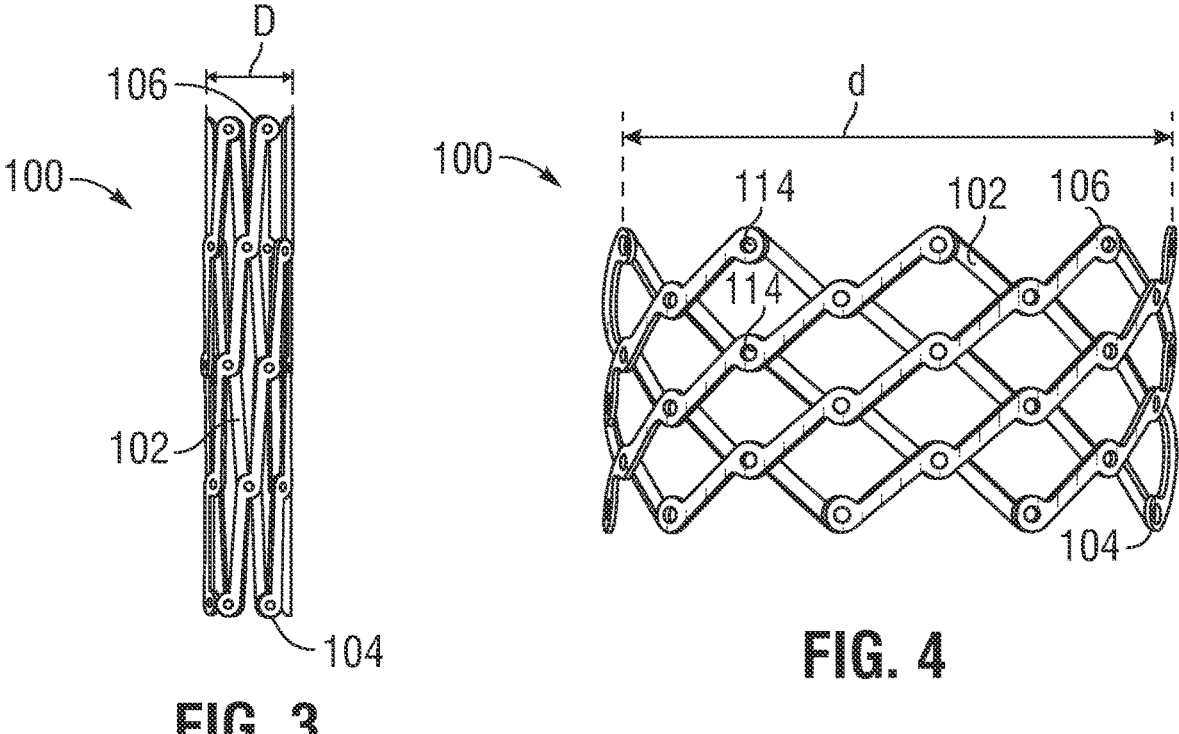
FIG. 3
FIG. 4

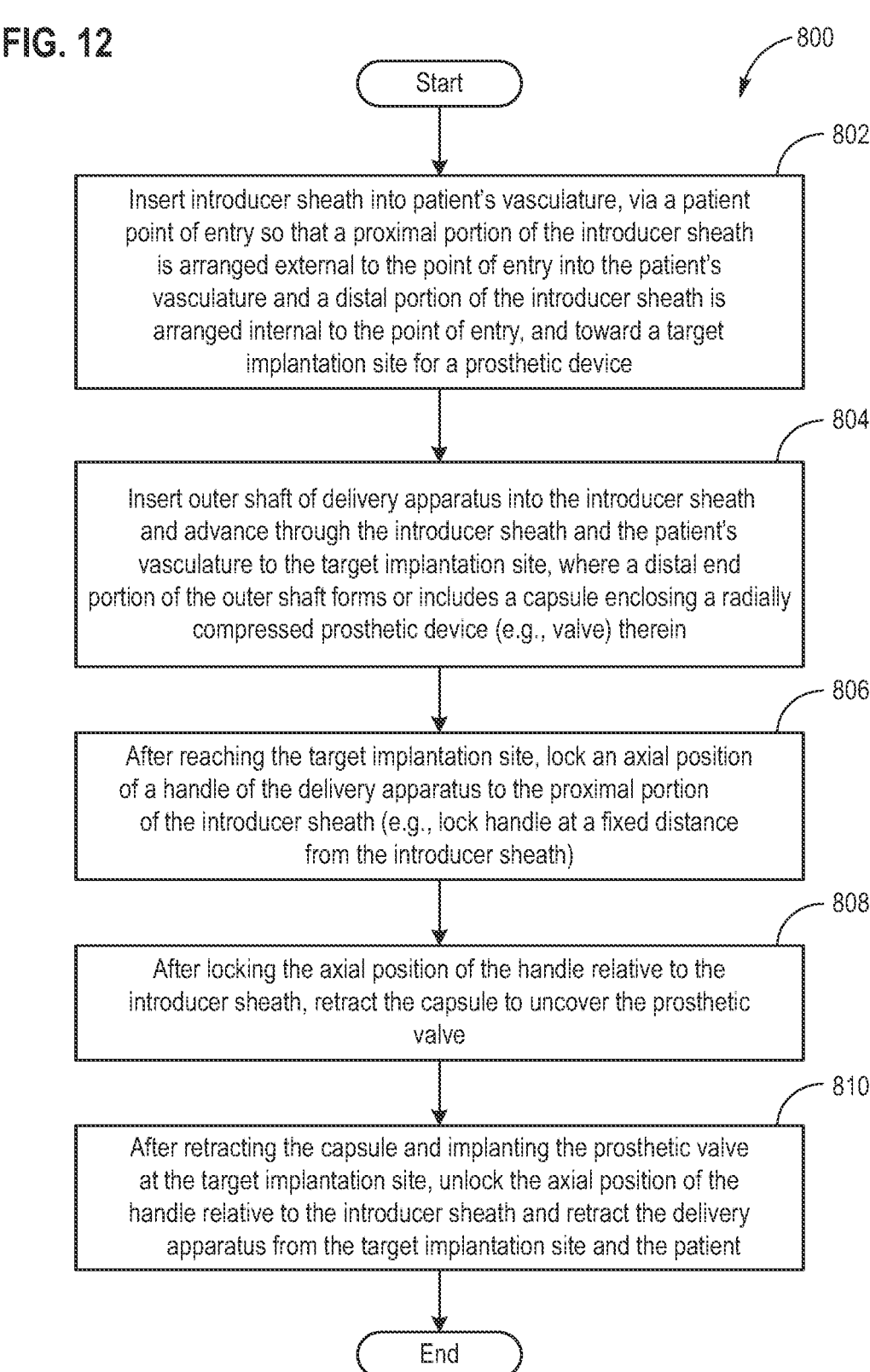

Start

802

Insert introducer sheath into patient's vasculature, via a patient
point of entry so that a proximal portion of the introducer sheath
is arranged external to the point of entry into the patient's
vasculature and a distal portion of the introducer sheath is
arranged internal to the point of entry, and toward a target
implantation site for a prosthetic device

804

Insert outer shaft of delivery apparatus into the introducer sheath
and advance through the introducer sheath and the patient's
vasculature to the target implantation site, where a distal end
portion of the outer shaft forms or includes a capsule enclosing a radially
compressed prosthetic device (e.g., valve) therein

806

After reaching the target implantation site, lock an axial position
of a handle of the delivery apparatus to the proximal portion
of the introducer sheath (e.g., lock handle at a fixed distance
from the introducer sheath)

808

After locking the axial position of the handle relative to the
introducer sheath, retract the capsule to uncover the prosthetic
valve

810

After retracting the capsule and implanting the prosthetic valve
at the target implantation site, unlock the axial position of the
handle relative to the introducer sheath and retract the delivery
apparatus from the target implantation site and the patient End

HANDLE LOCKING MECHANISMS FOR A TRANSCATHETER DELIVERY SYSTEM

CROSS REFERENCE TO RELATED APPLICATION

This application is a continuation of a PCT Patent Application No. PCT/US2021/012156, entitled "HANDLE LOCKING MECHANISMS FOR A TRANSCATHETER DELIVERY SYSTEM," filed Jan. 5, 2021, which claims the benefit of U.S. Provisional Patent Application No. 62/960, 516, entitled "HANDLE LOCKING MECHANISMS FOR A TRANSCATHETER DELIVERY SYSTEM," filed Jan. 13, 2020, all of which are incorporated by reference herein in their entirety.

FIELD

The present disclosure concerns embodiments of systems, and related methods, for locking an axial position of a handle of a transcatheter delivery apparatus relative to an introducer sheath during retraction of an outer shaft of the delivery apparatus to uncover a prosthetic valve mounted on a distal end of the delivery apparatus.

BACKGROUND

Endovascular delivery systems or devices are used in various procedures to deliver prosthetic medical devices or instruments to locations inside the body that are not readily accessible by surgery or where access without surgery is desirable. Access to a target location inside the body can be achieved by inserting and guiding a portion of the delivery device through a pathway or lumen in the body, including, but not limited to, a blood vessel, an esophagus, a trachea, any portion of the gastrointestinal tract, and a lymphatic vessel, to name a few. In one specific example, a prosthetic heart valve can be mounted in or on the distal end of a transcatheter delivery device and advanced through the patient's vasculature (e.g., through a femoral artery and the aorta) until the prosthetic valve reaches the target implantation site in the heart.

An introducer sheath may be used for introducing the delivery device into the patient's vasculature. The introducer sheath may include an elongated sleeve that is inserted into the vasculature via a patient point of entry and extends a distance into the patient's vasculature. In some embodiments, the delivery device may include a delivery device catheter (e.g., a series of coaxial shafts) that carry the prosthetic valve in a radially compressed (e.g., crimped) state at its distal end and a handle which controls the catheter and remains exterior to the patient point of entry.

The prosthetic valve may be covered in the crimped state by a capsule at the distal end of an outer shaft of the delivery device catheter, which is retracted once the prosthetic valve is positioned at the target implantation site. After retracting the capsule to uncover the prosthetic valve, the prosthetic valve may be expanded against the native anatomy at the target implantation site. Proper axial positioning, relative to a central longitudinal axis of the delivery device, of the prosthetic valve at the target implantation site is important for proper placement and functioning of the prosthetic valve. However, axial movement of the handle of the delivery device, which is attached to the capsule and the delivery device catheter, may cause the prosthetic valve to shift from its original or intended position at the target implantation site. For example, the inventors herein have recognized that during retraction of the outer shaft with the capsule, to expose the prosthetic valve, a proximal region of the delivery device catheter (in particular, the outer shaft) may rub against an interior of the introducer sheath, which may cause displacement of the entire delivery device, thereby requiring the user (e.g., clinician) to readjust the position of the prosthetic valve at the target implantation site (for example, move the prosthetic valve axially in a proximal or distal direction via the handle).

As such, there is a need for improved systems and methods for maintaining the prosthetic valve in a desired position at the target implantation site, by preventing unwanted axial movement of the delivery device during capsule retraction.

SUMMARY

Disclosed herein are locking mechanisms for transcatheter delivery systems, assemblies including a locking mechanism, a delivery apparatus, and introducer sheath, and related methods for locking an axial position of a handle of a delivery apparatus, the delivery apparatus configured to deliver a prosthetic valve to a target implantation site in a patient, relative to a proximal portion of an introducer sheath. The delivery apparatus can be used to deliver an implantable medical device, such as a prosthetic heart valve, to a target site in a patient, such as a heart. In some embodiments, assemblies including the delivery apparatus may further include an introducer sheath inserted into a lumen of a patient, such as vasculature, along a path to the target site. The delivery apparatus may then be advanced through an interior of the introducer sheath, to the target site. A handle of the delivery apparatus may control a position and operation of a remainder of the delivery apparatus.

In some embodiments, a locking mechanism may be configured to lock (e.g., fix) an axial position of a handle of the delivery apparatus, relative to a central longitudinal axis of the delivery apparatus, at a fixed distance from a patient point of entry and/or a proximal portion of an introducer sheath (which may be arranged proximate to the patient point of entry) during a portion of an implantation procedure. For example, after a distal end of the delivery apparatus including a capsule, the capsule containing a radially compressed prosthetic valve therein, reaches the target implantation site, and prior to retraction of the capsule, the locking mechanism may be used to lock the axial position of the handle relative to the patient point of entry and/or the introducer sheath. As a result, the handle cannot move axially relative to the patient point of entry, thereby maintaining a desired axial position of the prosthetic valve. After the handle is fixed with the locking mechanism, the capsule may be retracted to uncover the prosthetic valve. In some embodiments, the locking mechanism may comprise a locking arm adapted to couple to each of the introducer sheath and the handle of the delivery apparatus.

In one representative embodiment, a locking mechanism for a transcatheter delivery system, comprises: a first fixing member configured to be coupled to an introducer sheath of the transcatheter delivery system, the introducer sheath configured to receive a portion of a delivery apparatus of the transcatheter delivery system therein; a second fixing member configured to be coupled to a handle of the delivery apparatus; and a locking arm configured to be removably coupled at a first end to one of the first fixing member and the second fixing member and fixedly or removably coupled at a second end to another one of the first fixing member and the second fixing member, wherein the locking arm is moveable between a first position where an axial position, relative to a central longitudinal axis of the transcatheter delivery system, of the second fixing member is not fixed relative to the first fixing member via the locking arm and a second position where the axial position of the second fixing member is fixed relative to the first fixing member via the locking arm.

In another representative embodiment, a method comprises: advancing a portion of a transcatheter delivery apparatus through an introducer sheath inserted into a vessel of a patient and to a target implantation site for a prosthetic valve, wherein a distal end portion of an outer shaft of the delivery apparatus forms a capsule enclosing the prosthetic valve in a radially compressed state and wherein the introducer sheath includes a proximal portion arranged external to a point of entry into the vessel of the patient and a distal portion arranged internal to the point of entry; and after the distal end portion of the outer shaft of the delivery apparatus reaches the target implantation site and prior to retracting the capsule to uncover the prosthetic valve, locking an axial position of a handle of the delivery apparatus relative to the proximal portion of the introducer sheath via a locking mechanism configured to couple to each of the handle and the proximal portion of the introducer sheath, wherein the handle is arranged external to the point of entry.

In yet another representative embodiment, an assembly comprises: an introducer sheath; a delivery apparatus including a handle and an outer shaft that is coupled to and movable, in an axial direction arranged along a central longitudinal axis of the delivery apparatus, relative to the handle; and a locking mechanism, comprising: a locking arm having a first end portion fixedly coupled to a proximal portion of the introducer sheath and a second end portion configured to be removably coupled to the handle, wherein the locking arm is movable between an unlocked, first position where the second end portion is not rigidly coupled to the handle and the handle is able to move, in the axial direction, relative to the proximal portion of the introducer sheath and a locked, second position where the second end portion is rigidly coupled to the handle and the handle is maintained at a fixed distance, in the axial direction, from the proximal portion of the introducer sheath.

The foregoing and other objects, features, and advantages of the disclosed technology will become more apparent from the following detailed description, which proceeds with reference to the accompanying figures.

BRIEF DESCRIPTION OF THE DRAWINGS

FIG. 2 is a perspective view of a portion of another exemplary embodiment of a prosthetic heart valve.

FIG. 3 is a side view of the frame of the prosthetic heart valve of FIG. 2, shown in a radially collapsed configuration.

FIG. 4 is a side view of the frame of the prosthetic heart valve of FIG. 2, shown in a radially expanded configuration.

FIG. 7 is a side view of an embodiment of an introducer sheath shown being used for introducing the delivery apparatus of FIGS. 5 and 6 into a patient's vasculature.

FIG. 12 is a flow chart of a method for locking a handle of a delivery apparatus, the delivery apparatus configured to deliver a prosthetic medical device to a target implantation site in a patient, at a fixed distance, in an axial direction, relative to an introducer sheath used to introduce the delivery apparatus into the vasculature of the patient.

DETAILED DESCRIPTION

General Considerations

Figure 1:
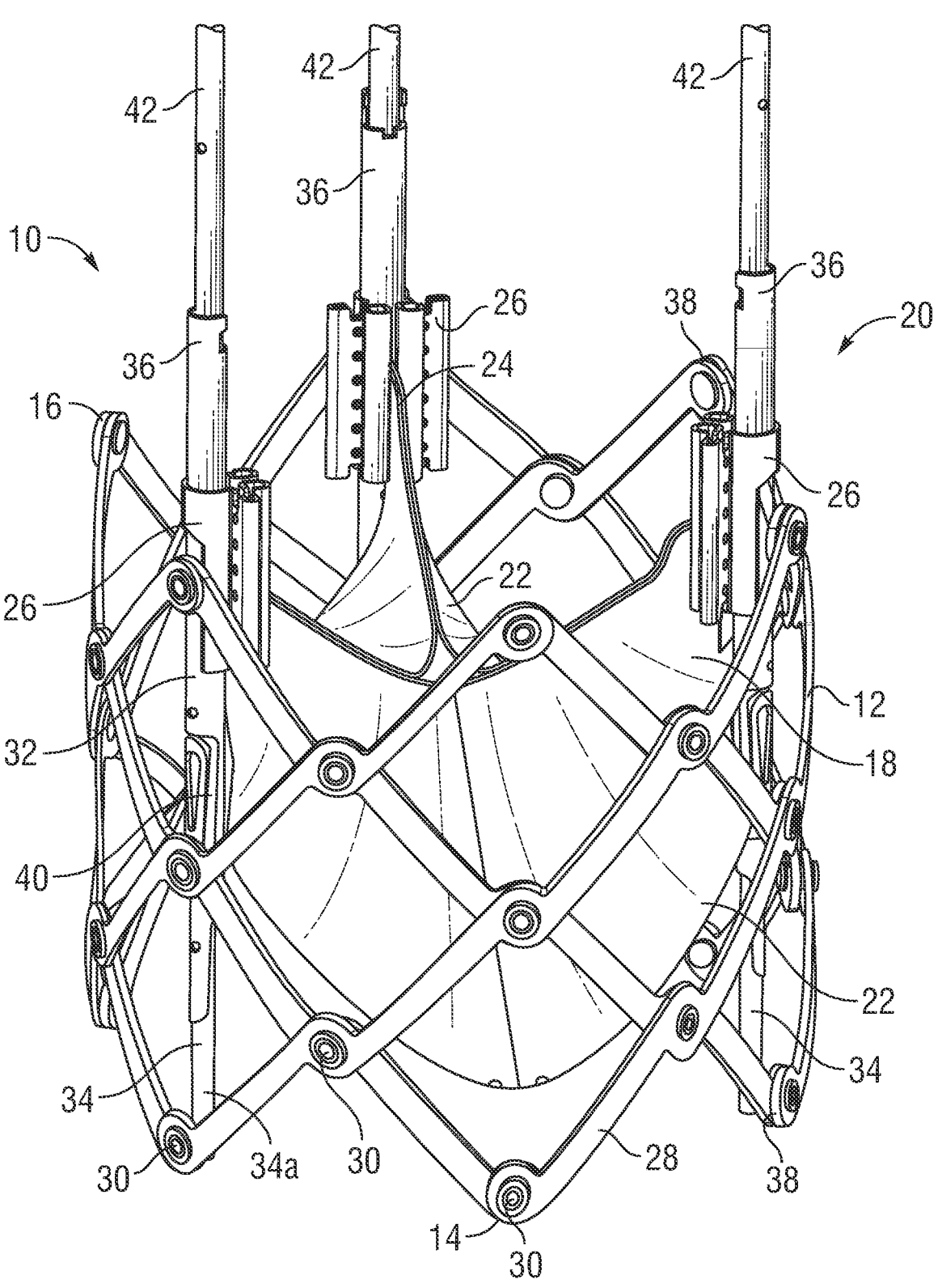
FIG. 1 is a perspective view of an exemplary embodiment of a prosthetic heart valve.

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

In the context of the present application, the terms "lower" and "upper" are used interchangeably with the term's "inflow" and "outflow", respectively. Thus, for example, the lower end of the valve is its inflow end and the upper end of the valve is its outflow end.

As used herein, with reference to the prosthetic heart valve and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Examples of the Disclosed Technology

Described herein are examples of assemblies including a prosthetic valve, delivery apparatus, introducer sheath, and locking mechanism, and related methods for delivering a prosthetic valve to and implanting the prosthetic valve at a target implantation site with the delivery apparatus. The delivery apparatuses (e.g., devices), introducer sheaths, and locking mechanisms may include proximal portions (e.g., ends) and distal portions (e.g., ends). As used herein, the "distal end" or "distal portion" of one of these components may refer to the portion or end of the component that is positioned farthest away from a handle of the delivery apparatus and closest to the target implantation site while the "proximal end" or "proximal portion" of one of these components may refer to the portion or end of the components that is positioned closest to the handle and farthest away from the target implantation site. For example, the distal end of the delivery apparatus may be oriented further downstream than the proximal end of the delivery apparatus when the delivery apparatus is being advanced through a lumen of a patient, toward the target implantation site.

The delivery apparatus may include an outer shaft extending from a handle of the delivery apparatus. A distal end portion of the outer shaft forms a sheath (e.g., capsule) adapted to enclose the prosthetic valve therein in a radially compressed configuration during advancement of the delivery apparatus to the target implantation site. The delivery apparatus may further include an inner shaft arranged within the outer shaft and including a nosecone arranged at a distal end of the inner shaft, the nosecone arranged outside of the outer shaft, at the distal end portion of the outer shaft (while the outer shaft is covering the prosthetic valve). The outer shaft, and additional components of the delivery apparatus arranged within the outer shaft, may be advanced through an introducer sheath inserted into the vasculature of the patient. The introducer sheath enters the patient's vasculature via a patient point of entry and extends a distance into the vasculature from the point of entry. A proximal portion of the introducer sheath and a handle of the delivery apparatus can each be arranged exterior to the patient point of entry.

In some embodiments, a locking mechanism can be configured to attach to each of the proximal portion of the introducer sheath and the handle of the delivery apparatus during at least a portion of the implantation procedure. In some embodiments, the locking mechanism comprises a locking arm fixed to the introducer sheath via one or more components of the locking mechanism and removably coupled to the handle via one or more components. For example, the locking mechanism can comprise a clamp attached to the handle and configured to removably couple a proximal portion of the locking arm.

In some embodiments, once the radially compressed prosthetic valve reaches the target implantation site (within the capsule), the locking mechanism can be adjusted such that the locking arm is fixed to both the proximal portion of the introducer sheath and the handle. As a result, the axial position of the handle is locked (e.g., fixed) relative to the introducer sheath. Thus, the handle may not move in the axial direction relative to the introducer sheath and the patient point of entry, thereby causing the prosthetic valve to remain at a desired position at the target implantation site. The capsule may then be retracted to uncover the prosthetic valve. After retracting the capsule and/or implantation the prosthetic valve at the target implantation site, the locking mechanism may be adjusted to release the handle such that it may move axially relative to the introducer sheath. The delivery apparatus may then be removed (e.g., retracted) from the patient.

The prosthetic valves disclosed herein can be radially compressible and expandable between a radially compressed configuration and a radially expanded configuration. Thus, the prosthetic valves can be crimped on an implant delivery apparatus (e.g., device) in the radially compressed configuration during delivery, and then expanded to the radially expanded configuration once the prosthetic valve reaches the implantation site.

FIG. 1 shows an exemplary prosthetic valve 10, according to one embodiment. The prosthetic valve 10 can be radially compressible and expandable between a radially compressed configuration for delivery into a patient (see e.g., FIG. 3) and a radially expanded configuration (see e.g., FIGS. 1 and 4). In particular embodiments, the prosthetic valve 10 can be implanted within the native aortic annulus, although it also can be implanted at other locations in the heart, including within the native mitral valve, the native pulmonary valve, and the native tricuspid valve. The prosthetic valve 10 can include an annular stent or frame 12 having a first (e.g., inflow) end 14 and a second (e.g., outflow) end 16.

In the depicted embodiments, the first end 14 is an inflow end and the second end 16 is an outflow end. The outflow end 16 can be coupled to a delivery apparatus for delivering and implanting the prosthetic valve within the native aortic valve is a transfemoral, retrograde delivery approach. Thus, in the delivery configuration of the prosthetic valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore is the proximal-most end of the prosthetic valve in the delivery configuration) when delivering the prosthetic valve to the native mitral valve via a trans-septal delivery approach.

The prosthetic valve 10 can also include a valvular structure 18 which is coupled to the frame 12 and configured to regulate the flow of blood through the prosthetic valve 10 from the inflow end to the outflow end. The prosthetic valve 10 can further include a plurality of actuators 20 mounted to and equally spaced around the inner surface of the frame 12. Each of the actuators 20 can be configured to form a releasable connection with one or more respective actuators of a delivery apparatus, as further described below.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). The leaflets 22 can be arranged to form commissures 24, which can be, for example, mounted to respective actuators 20. Further details regarding transcatheter prosthetic heart valves, including the manner in which the valvular structure can be coupled to the frame 12 of the prosthetic valve 10, can be found, for example, in U.S. Pat. Nos. 6,730,118, 7,393,360, 7,510,575, 7,993,394, and 8,652,202, and U.S. Patent Application Publication No. 2018/0325665, all of which are incorporated herein by reference in their entireties.

In some embodiments, the prosthetic valve 10 can include a plurality of commissure support elements configured as commissure clasps or clamps 26. In the illustrated configuration, the prosthetic valve includes a commissure clamp 26 positioned at each commissure 24 and configured to grip adjacent portions of two leaflets 22 at each commissure 24, at a location spaced radially inwardly of the frame 12. Each clamp 26 can be mounted on an actuator 20 as shown. In alternative embodiments, the commissure supports elements (such as clamps 26) can be mounted to the struts 28 of the frame, or alternatively, the commissures 24 can be mounted (e.g., sutured) directly to the struts of the frame. Further details of the commissure clamps 26 and other techniques for mounting the commissures of a valve assembly to a frame can be found in U.S. Patent Application Publication No. 2018/0325665.

Although not shown, the prosthetic valve 10 can also include one or more skirts or sealing members. For example, the prosthetic valve 10 can include an inner skirt mounted on the inner surface of the frame. The inner skirt can function as a sealing member to prevent or decrease perivalvular leakage, to anchor the leaflets 22 to the frame, and/or to protect the leaflets against damage caused by contact with the frame during crimping and during working cycles of the prosthetic valve. The prosthetic valve 10 can also include an outer skirt mounted on the outer surface of the frame 12. The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic valve 10 when the prosthetic valve 10 is in the expanded configuration. In other implementations, the struts 28 can be offset by a different amount than depicted in FIG. 1, or some or all of the struts 28 can be positioned parallel to the longitudinal axis of the prosthetic valve 10.

In the illustrated embodiment, the struts 28 are pivotably coupled to one another at one or more pivot joints along the length of each strut. For example, in the illustrated configuration, each of the struts 28 can be formed with apertures (see e.g., apertures 114 in FIG. 4) at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. patent application Ser. Nos. 15/831,197; 62/515,437; 62/548,855, all of which are incorporated herein by reference. Additional examples of expandable prosthetic valves that can be used with the delivery apparatuses and systems disclosed herein are described in U.S. Publication No. 2015/0135506 and 2014/0296962, which are incorporated herein by reference.

Referring still to FIG. 1, in some embodiments, the prosthetic valve 10 can comprise one or more actuators 20 configured to produce radial expansion and compression of the frame. The one or more actuators in the illustrated embodiment comprise one or more push-pull mechanisms 32 coupled to the frame 12. In the illustrated embodiment, the prosthetic valve 10 has three push-pull mechanisms 32, however, in other embodiments a greater or fewer number of push-pull mechanisms 32 can be used.

Each push-pull mechanism 32 can generally comprise an inner member 34, such as an inner tubular member, and an outer member 36 disposed about the inner member 34. The inner members 34 and the outer members 36 can be movable longitudinally relative to each other in a telescoping manner to radially expand and contract the frame 12, as further described in U.S. Patent Application No. 62/430,810, Ser. Nos. 15/831,197 and 15/978,459, which are incorporated herein by reference. The inner members 34 can be, for example, rods, cables, wires, or tubes. The outer members 36 can be, for example, tubes or sheaths having sufficient rigidity such that they can apply a distally directed force to the frame without bending or buckling.

The inner members 34 can have distal end portions 34a coupled to the inflow end 14 of the frame 12 (e.g., with a coupling element such as a pin member or pin 30). In the illustrated embodiment, each of the inner members 34 are coupled to the frame at respective apices 38 at the inflow end 14 of the frame 12. For example, the distal end portion 34a of each inner member 34 can be pivotably connected to the rivet or pin 30 that connects the two struts at the adjacent apex 38. The outer members 36 can be coupled to apices 38 at the outflow end 16 of the frame 12 at, for example, a mid-portion of the outer member 36, as shown in FIG. 1, or at a proximal end portion of the outer member, as desired. The outer members 36 can be pivotably connected to the rivet or pin 30 that connects the two struts at the adjacent apex 38.

The inner member 34 and the outer member 36 can telescope relative to each other between a fully contracted state (corresponding to a fully radially expanded state of the prosthetic valve) and a fully extended state (corresponding to a fully radially compressed state of the prosthetic valve). In the fully extended state, the inner member 34 is fully extended from the outer member 36. In this manner, the push-pull mechanisms 32 allow the prosthetic valve to be fully expanded or partially expanded to different diameters and retain the prosthetic valve in the partially or fully expanded state. It should be understood that the inner members 34 and the outer members 36 can be coupled to other locations on the frame to produce radial compression and expansion of the frame, so long as the inner member and outer member of each actuator are coupled at axial spaced pivot joints of the frame.

In use, a delivery apparatus, such as example delivery apparatus 300 shown in FIGS. 5-6, as described further below, can be releasably coupled to the push-pull mechanisms 32 of prosthetic valve 10. For example, the delivery apparatus can have one or more actuator assemblies that are releasably coupled to respective push-pull mechanisms 32 of the prosthetic valve. The actuators (e.g., actuator assemblies) of the delivery apparatus can be configured to transfer pushing and/or pulling forces from a handle of the delivery apparatus to the push-pull mechanisms 32 of the prosthetic valve. Each of the actuator assemblies of the delivery apparatus can include an inner member 42 that is releasably coupled to a respective inner member 34 of a push-pull mechanism 32. Each actuator assembly of the delivery apparatus can also include an outer member (not shown) that is releasably coupled to a respective outer member 36 of a push-pull mechanism 32.

Once coupled to the delivery apparatus, the prosthetic valve 10 can then be radially collapsed (see e.g., FIG. 3) and the distal end portion of the delivery apparatus, along with the radially collapsed valve, can be inserted into a patient. Once the prosthetic valve 10 is at the desired implantation site, the prosthetic valve can be radially expanded (see e.g., FIG. 4). In some embodiments, as shown in FIG. 1, the push-pull mechanisms 32 can comprise one or more locking mechanisms 40, allowing the frame 12 to maintain an expanded diameter after the prosthetic valve is released from the delivery apparatus. Additional details of the locking mechanism can be found in U.S. Patent Application Publication No. 2018/0325665.

FIG. 2 illustrates a medical assembly, according to another embodiment. The assembly comprises a prosthetic valve 100 and one or more linear actuator assemblies 200 (one shown in FIG. 2) releasably coupled to the prosthetic valve. The prosthetic valve 100 comprises a frame 102. The prosthetic valve 100 can include leaflets and inner and/or outer skirts as previously described, although these components are omitted for purposes of illustration. The frame 102 comprises a plurality of struts 116 formed with apertures 114 (see FIG. 4) and pivot members 118 (e.g., pins or rivets) connecting the struts to each other form a plurality of pivot joints. The frame 102 can have the same construction as the frame 12, except that the frame 102 includes struts 116 that are longer than struts 28 of frame 12. The longer struts 116 form more pivot joints along the length of each strut and more openings or cells of the frame compared to the struts 28.

FIGS. 3-4 illustrate the bare frame 102 (without the leaflets and other components) of the prosthetic valve 100 for purposes of illustrating expansion of the prosthetic valve from the radially compressed configuration to the radially expanded configuration. FIG. 3 shows the frame 102 in the radially compressed configuration (having diameter D), and FIG. 4 shows the frame 102 in the fully radially expanded configuration (having diameter d). The prosthetic valve 100 in the illustrated configuration can be radially expanded by maintaining the first end 104 of the frame 102 at a fixed position while applying a force in the axial direction against the second end 106 toward the first end 104. Alternatively, the prosthetic valve 100 can be expanded by applying an axial force against the first end 104 while maintaining the second end 106 at a fixed position, or by applying opposing axial forces to the first and second ends 104 and 106, respectively.

The one or more actuator assemblies 200 can be components of a delivery apparatus (e.g., the delivery apparatus 300 of FIGS. 5-6) and are configured to produce radial expansion and compression of the frame 102. FIG. 2 shows a linear actuator assembly 200 in the process of being disconnected from the frame 102 after the frame has been radially expanded. As shown, the actuator assembly 200 can include an inner actuator member 202 (which can also be referred to as an actuation member), a cover tube 204 extending co-axially over the actuator member 202, a support tube or pusher member 206 extending co-axially over the cover tube 204, a threaded screw 208. The actuator member 202 can be, for example, a rod, cable, or wire. The actuator member 202 can be connected at its distal end to the threaded screw 208 such that rotation of the actuator member 202 causes rotation of the threaded screw 208. The proximal end of the actuator member 202 can be connected to a handle or other control device (not shown) of the delivery apparatus that a doctor or operator of the delivery apparatus can use to rotate the actuator member 202. Similarly, the proximal ends of each cover tube 204 and each support tube 206 can be connected to the handle. For each actuator assembly 200, a pair of a threaded nut or sleeve 110 and a stopper 112 can be affixed to the frame at axially spaced locations, such as at locations at or adjacent the distal and proximal ends of the frame.

The screw 208 has an externally threaded surface that can engage an internally threaded surface of the sleeve 110, which is affixed to the frame 102, such as at the distal end of the frame. When the actuator member 202 is rotated to screw the screw 208 into the sleeve 110, the actuator member 202 becomes connected to the distal end of the frame 102 such that proximal or distal motion of the actuator member 202 causes proximal or distal motion, respectively, of the distal end of the frame 102.

The cover tube 204 annularly surrounds the actuator member 202. The cover tube 204 can be connected to the actuator member 202 such that the actuator member 202 and the cover tube 204 rotate together and move axially together. The actuator member 202 and the cover tube 204 extend through the stopper 112, which can be affixed to a proximal end of the frame. The support tube 206 annularly surrounds the cover tube 154. The stopper 112 has an annular inner surface with an inner diameter larger than the outer diameter of the cover tube 204 and the screw 208 such that the cover tube 204 and the screw 208 can be retracted through the stopper 112 as the frame 102 is expanded and once the actuator is retracted proximally by the user to disconnect it from the frame. The stopper 112 is sized to abut or engage the distal end of the support tube 206 such that the support tube 206 is prevented from moving distally beyond the stopper 112.

In operation, prior to implantation in a patient, the screw 208 is threaded into the sleeve 110, thereby connecting the linear actuator assembly 200 to the frame 102. The frame 102 can then be placed in a radially collapsed state and the prosthetic valve and the distal end portion of the delivery apparatus can be inserted in a patient. Once the prosthetic valve 100 is at a desired implantation site, the frame 102 can be radially expanded as described herein.

To radially expand the frame 102, the support tube 206 is held firmly against the stopper 112. The actuator member 202 is then pulled in a proximal direction through the support tube 206, such as by pulling on the proximal end of the actuator member 202 or actuating a control knob on the handle that produces proximal movement of the actuator member 202. Because the support tube 206 is being held against the stopper 112, which is connected to the proximal end of the frame 102, the proximal end of the frame 102 is prevented from moving relative to the support tube 206 and the handle. As such, movement of the actuator member 202 in a proximal direction results in movement of the distal end of the frame 102 in a proximal direction causing the frame 102 to foreshorten axially and expand radially.

It should be understood that the frame 102 can also be radially expanded by pushing the proximal end of the frame toward the distal end of the frame by pushing the support tube 206 against the stopper 112 while keeping the actuator member 202 stationary relative to the handle, or alternatively, by simultaneously pushing the support tube 206 distally against the stopper 112 and pulling the actuator member 202 proximally.

After the frame 102 is expanded to a desired radially expanded size, one or more locking mechanisms can be actuated to lock the frame 102 in the desired radially expanded size, and the linear actuator assembly 200 can be disconnected from the frame 102. To disconnect the linear actuator assembly 200 from the frame 102, the actuator member 202 can be rotated so as to unscrew the screw 208 from the stopper 112. The actuator member 202 and the cover tube 204 can then be retracted proximally through the stopper 112 and the linear actuator assembly 200 (including the actuator member 202, the screw 208, the cover tube 204, and the support tube 206) can be withdrawn from the patient. The cover tube 204 facilitates passage of the screw 208 through the stopper 112. In some embodiments, the cover tube 204 can be excluded. In embodiments that have more than one linear actuator assembly 200, the above procedure for expanding the frame 102 is performed for each linear actuator assembly 150.

Further details of the actuator assemblies and various exemplary locking mechanisms can be found in U.S. Publication No. 2018/0153689.

Figures 5, 6:
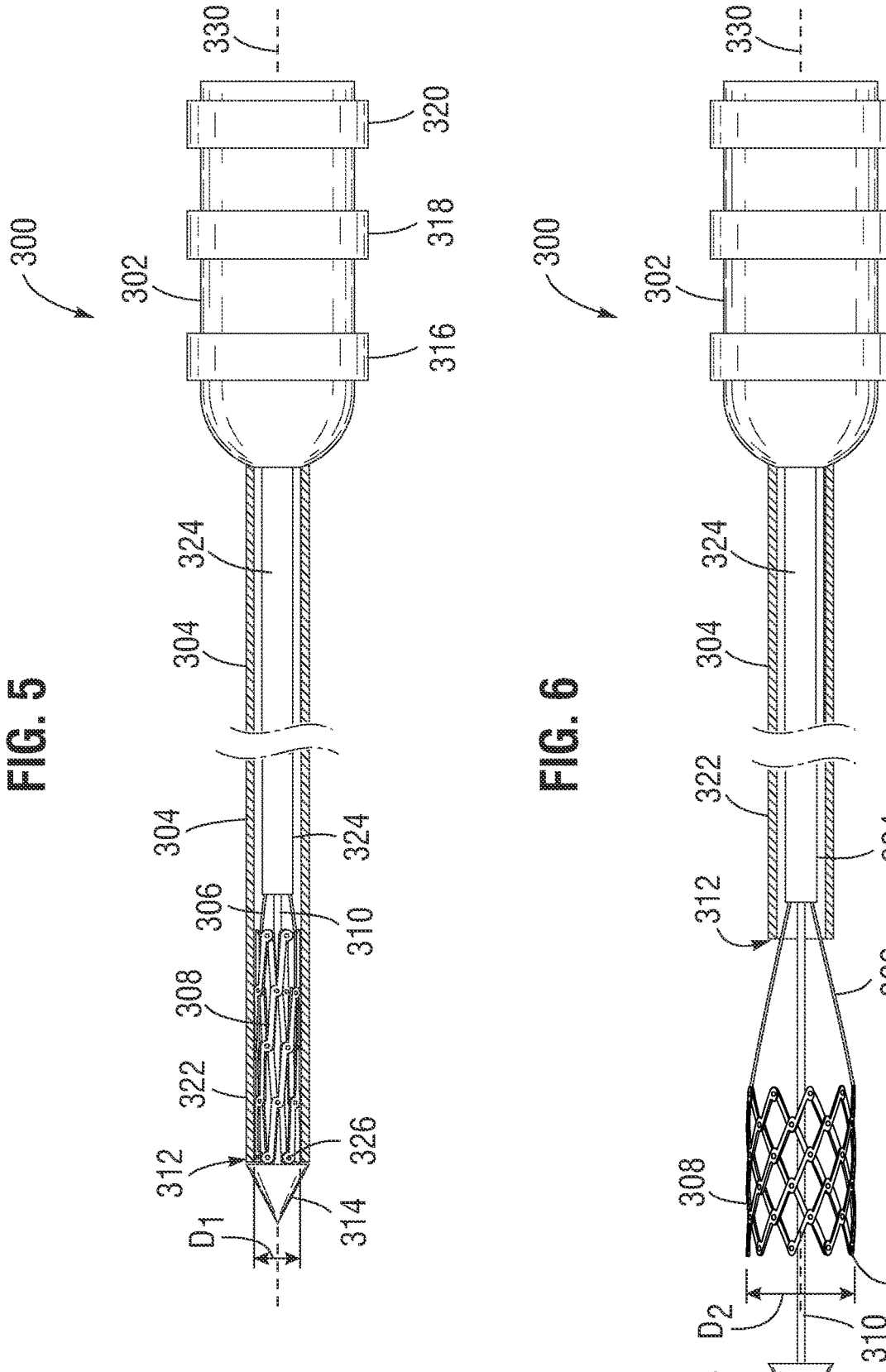
FIG. 5 is a side view of an embodiment of a transcatheter delivery apparatus for delivering a prosthetic heart valve to a target implantation site, with the prosthetic heart valve retained in a radially compressed state within a capsule of the delivery apparatus.
FIG. 6 is a side view of the transcatheter delivery apparatus of FIG. 5, with the capsule retracted to uncover the prosthetic heart valve.

FIGS. 5-6 illustrate a delivery apparatus 300, according to one embodiment, adapted to deliver a prosthetic heart valve (e.g., prosthetic valve) 308, such as the prosthetic valve 100 illustrated in FIGS. 2-4 and/or the prosthetic valve 10 illustrated in FIG. 1, as described above, to a target implantation site in a patient. FIGS. 5-6 show the prosthetic valve 308 in different configurations relative to the delivery apparatus 300 during a valve implantation procedure. The prosthetic valve 308 can be releasably coupled to one or more components of the delivery apparatus 300, as described further below. It should be understood that the delivery apparatus 300 and other delivery systems and/or apparatuses disclosed herein can be used to implant prosthetic devices other than prosthetic valves, such as stents or grafts.

The delivery apparatus 300 in the illustrated embodiment generally includes a handle 302, an elongate shaft 304 (which comprises an outer, or outermost, shaft in the illustrated embodiment) extending distally from the handle 302, an inner (e.g., innermost) shaft 310, an intermediate shaft 324 arranged coaxial with and between (in the radial direction which is perpendicular to a central longitudinal axis 330 of the delivery apparatus 300) the outer shaft 304 and the inner shaft 310, and at least one actuator assembly (e.g., member or actuator) 306 for expanding and compressing the prosthetic valve 308, the at least one actuator assembly 306 extending through the outer shaft 304 and distally outwardly from a distal end portion 312 of the outer shaft 304.

In some embodiments, the outer shaft 304, inner shaft 310, intermediate shaft 324, and/or actuator assembly 306 may make up a delivery apparatus catheter of the delivery apparatus 300, controlled by and attached to the handle 302.

The delivery apparatus 300 can include three actuator assemblies 306 (only two of the three are shown in FIGS. 5-6) releasably coupled to the prosthetic valve 308. However, in alternate embodiments, the delivery apparatus 300 may include more or less than three actuator assemblies 306 (e.g., one, two, four, or the like). As shown in FIGS. 5-6, the plurality of actuator assemblies 306 are circumferentially spaced apart from each other around a circumference of the delivery apparatus 300 and can extend axially through the outer shaft 304 from the handle 302 to the prosthetic valve 308.

In particular embodiments, each actuator assembly 306 can be releasably coupled to a corresponding actuator of the prosthetic valve (e.g., an actuator 32 as shown in FIG. 1). Each actuator assembly 306 can include an inner member (similar to inner member 42 shown in FIG. 1) having a distal end releasably coupled to an inner member 34 of an actuator (e.g., push-pull mechanism 32) and an outer member having a distal end releasably coupled to an outer member 36 of an actuator (e.g., push-pull mechanism 32). In another embodiment, each actuator assembly 306 can be an actuator assembly 200 releasably coupled to the prosthetic valve 308 via a threaded sleeve 110.

In some embodiments, the intermediate shaft 324 may be adapted to house and organize the actuator assemblies 306. For example, the actuator assemblies 306 may be housed within and extend outwardly from a distal end of the intermediate shaft 324. In some embodiments, each actuator assembly 306 may be kept separate from the other actuator assemblies 306 within the intermediate shaft 324. For example, each actuator assembly 306 can extend through a separate lumen of the intermediate shaft 324.

As shown in FIGS. 5-6, a distal end of the inner shaft 310 may include a nosecone 314 which may be used to guide the delivery apparatus 300 through a lumen of a patient to a target implantation site for the prosthetic valve 308. The nosecone 314 may be arranged proximate to a distal end 326 of the prosthetic valve 308.

In use, the delivery apparatus 300 can be releasably coupled to the prosthetic valve 308 to produce radial expansion and compression of the frame of the prosthetic valve 308. In some embodiments, the actuator assemblies 306 of the delivery apparatus 300 can be configured to transfer pushing and/or pulling forces from the handle 302 of the delivery apparatus 300 to the prosthetic valve 308. For example, in some embodiments, the actuator assemblies 306 may have distal end portions that can be releasably connected to the prosthetic valve 308 via respective release-and-locking units.

In some embodiments, the outer shaft 304 of the delivery apparatus 300 can be configured as a steerable guide catheter having an adjustable curvature for use in steering the delivery apparatus 300 through the patient's vasculature. In particular embodiments, the outer shaft 304 can include a steerable distal section, the curvature of which can be adjusted by the operator to assist in guiding the apparatus through the patient's vasculature.

The outer shaft 304 and the actuator assemblies 306 can be moved relative to one another (axially and/or rotationally) to facilitate delivery and positioning of the prosthetic valve 308 at an implantation site in the patient's body.

In some embodiments, the distal end portion 312 of the outer shaft 304 can form and/or function as a sheath (e.g., capsule) 322 that is sized and shaped to receive and house the prosthetic valve 308 in a radially compressed state for delivery into and through a patient's vasculature. Once the prosthetic valve 308 is advanced to the implantation site or adjacent the implantation site, the prosthetic valve 308 can be advanced from the capsule 322 by retracting the outer shaft 304, and thus the capsule 322, axially, along central longitudinal axis 330, relative to the actuator assemblies 306 and the prosthetic valve 308. As such, the prosthetic valve 308 may be uncovered while the capsule 322 moves axially back towards the handle 302 (e.g., in a proximal direction along the central longitudinal axis 330). In alternative embodiments, the prosthetic valve 308 can be advanced from the capsule 322 by advancing the actuator assemblies 306 relative to the outer shaft 304, after which the prosthetic valve 308 can be radially expanded.

The advancement of the prosthetic valve 308 from the sheath by axially moving the actuator assemblies 306 relative to the outer shaft 304 or by retracting the outer shaft 304 relative to the actuator assemblies 306 may be actuated by operating a first knob 316 on the handle 302. The first knob 316 can be operatively connected to a proximal end portion of the outer shaft 304 and can be configured to retract the outer shaft 304 proximally relative to the actuator assemblies 306 to deploy the prosthetic valve 308 from the distal end portion 312 of the capsule 322 or operatively connected to proximal ends of the actuator assemblies 306 to advance the actuator assemblies 306 distally relative to the outer shaft 304 to deploy the prosthetic valve 308 from the distal end portion 312 of the capsule 322. The first knob 316 may be a slidable or rotatable adjustment element that is operatively connected to the actuator assemblies 306 and/or the outer shaft 304.

The handle 302 may include additional adjustment knobs, such as a second knob 318 and a third knob 320, as shown in FIGS. 5-6. In some embodiments, the second knob 318 may be operatively coupled to the actuator assemblies 306 and actuate the actuator assemblies 306 to adjust the prosthetic valve 308 from a non-expanded (or radially compressed) configuration (as shown in FIG. 5, as described further below) to a radially expanded configuration, and vice versa.

In some embodiments, the third knob 320 may be operatively coupled to the actuator assemblies 306 and actuate the actuator assemblies 306 to disconnect from the prosthetic valve 308. As a result, the prosthetic valve 308 may be detached from the delivery apparatus 300 and implanted (e.g., deployed) at the target implantation site.

FIG. 5 shows the prosthetic valve 308 retained in a radially compressed state within the capsule 322 of the delivery apparatus 300. As such, in FIG. 5, the prosthetic valve 308 is in its radially compressed configuration having a smallest diameter, D1. The smallest diameter D1 may be approximately the same as an inner diameter of the capsule 322. The capsule 322 surrounding an outside of the prosthetic valve 308, as shown in FIG. 5, may maintain the prosthetic valve in the radially compressed configuration. As a result, the prosthetic valve 308 may be advanced through a patient's vasculature, for example, to the target implantation site via the delivery apparatus 300.

After reaching the target implantation site, the capsule 322 may be pulled (e.g., retracted) away from the nosecone 314 and the prosthetic valve 308, in a proximal direction along the central longitudinal axis 330 of the delivery apparatus 300, to uncover the prosthetic valve 308. In alternate embodiments, the actuator assemblies 306 may be advanced, in the distal direction, to move the prosthetic valve 308 out of the capsule 322. FIG. 6 shows the prosthetic valve 308 in the uncovered (e.g., unsheathed) state where it is arranged outside of the capsule 322. At this state, the prosthetic valve 308 is not actively expanded via the actuator assemblies 306. However, since it is no longer bound by (e.g., retained within) the capsule 322, the prosthetic valve 308 may assume a partially expanded diameter D2 which is larger than the smallest diameter D1 due to the inherent resiliency of the struts of the frame. For example, after being deployed from the capsule 322, the prosthetic valve 308 may expand, in the radial direction relative to the central longitudinal axis 330 of the prosthetic valve 308 and the delivery apparatus 300, by 10-20%. It should be noted that the extent of expansion of the prosthetic valve 308, from the compressed, smallest diameter D1 (FIG. 5) to the partially expanded diameter D2 (FIG. 6) may be exaggerated in FIG. 6 for the purposes of illustration.

Figure 7:
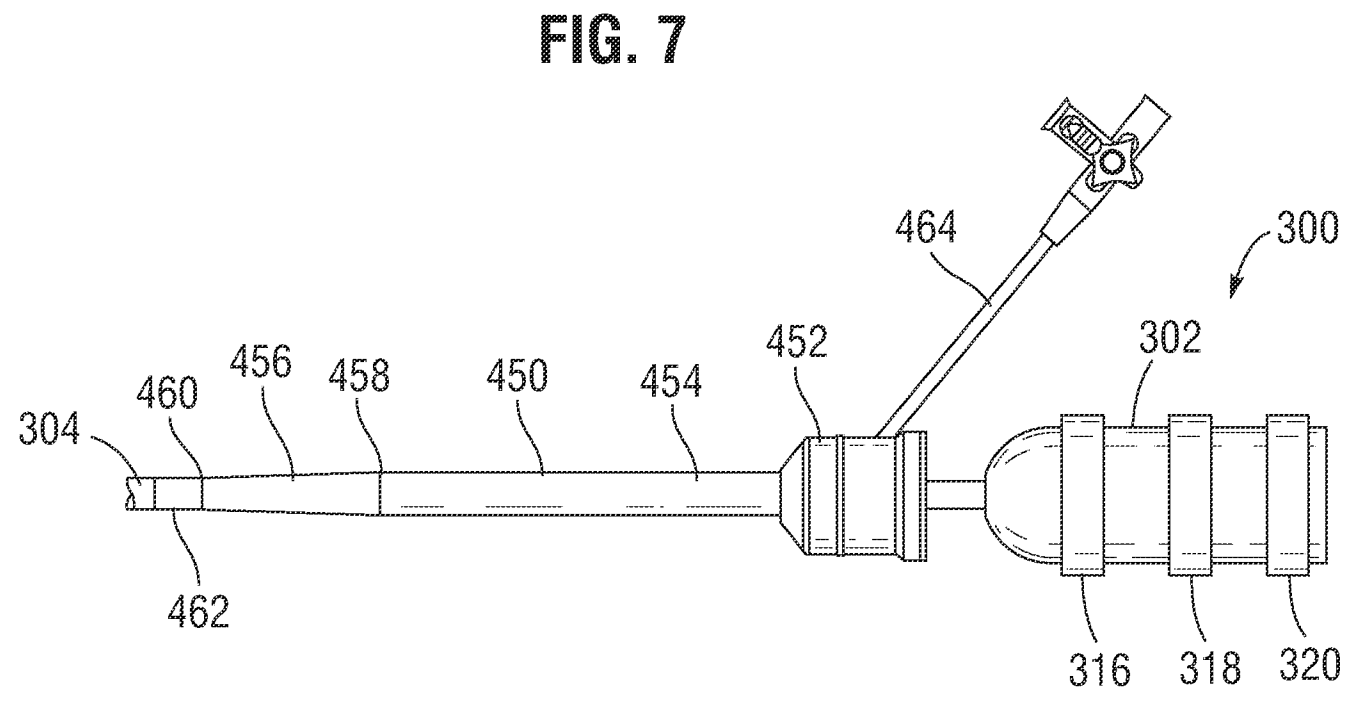

FIG. 7 shows an embodiment of an introducer sheath 450 which may be used to introduce a transcatheter delivery apparatus, such as the delivery apparatus 300 shown in FIGS. 5 and 6, into the body of a patient. A transcatheter delivery system can comprise the introducer sheath 450 and the delivery apparatus 300. The introducer sheath 450 in the illustrated embodiment includes an introducer housing (also referred to as a "hub") 452 and an introducer sleeve 454 extending from the housing 452. The housing 452 houses one or more valves. In one embodiment, the one or more valves may include a sealing valve. A flush port 464, which may include a stopcock, as shown in FIG. 7, can extend outward and away from the housing 452.

In use, the sleeve 454 is inserted into a body vessel (e.g., the femoral artery) while the housing 452 remains outside the body. In some embodiments, the housing 452 may be referred to as or be part of a proximal portion of the introducer sheath 450.

A delivery device, such as delivery apparatus 300, is inserted through a proximal opening in the housing 452, the one or more valves within the housing 452, the sleeve 454, and into the body vessel. The one or more valves of the housing 452 may sealingly engage the outer surface of the outer shaft 304 to minimize blood loss. In some applications, a loader device (not shown) can be placed over the distal end portion of the delivery device and the prosthetic valve before the distal end portion of the delivery device and the prosthetic valve are inserted into the housing 452. The loader device prevents the one or more valves inside the housing 452 from directly contacting the prosthetic valve as it is pushed through the introducer sheath.

The sleeve 454 can have a tapered portion 456 that tapers from a first diameter at a proximal end 458 to a second, smaller diameter at a distal end 460. A reduced diameter distal end portion 462 extends from the tapered portion 456 to the distal end of the sleeve 454. The tapered portion 456 provides for a smoother transition between the outer surface of the sleeve 454 and the outer surface of the outer shaft 304. The tapered portion 456 also allows for variable placement of the sleeve 454 in the patient's vasculature to help minimize complete occlusion of the femoral artery. In some embodiments, the sleeve 454 can be configured to locally expand as the prosthetic valve is advanced through the sleeve. Further details regarding an embodiment of the introducer sheath are disclosed in International Publication No. WO 2019/199692, which is incorporated herein by reference.

While FIG. 7 shows one example embodiment of an introducer sheath 450, in alternate embodiments, the transcatheter delivery apparatuses disclosed herein, such as delivery apparatus 300 shown in FIGS. 5 and 6, may be used with an introducer sheath having a different configuration (e.g., such as a different overall shape, different components, and the like). Further, in alternate embodiments, the delivery apparatus 300 may include additional or different components than those shown in FIGS. 5 and 6. As such, FIGS. 5-7 show one example embodiment of a (transcatheter) delivery apparatus and introducer sheath that may be used to deliver a prosthetic heart valve to a target implantation site.

Figures 8, 9:
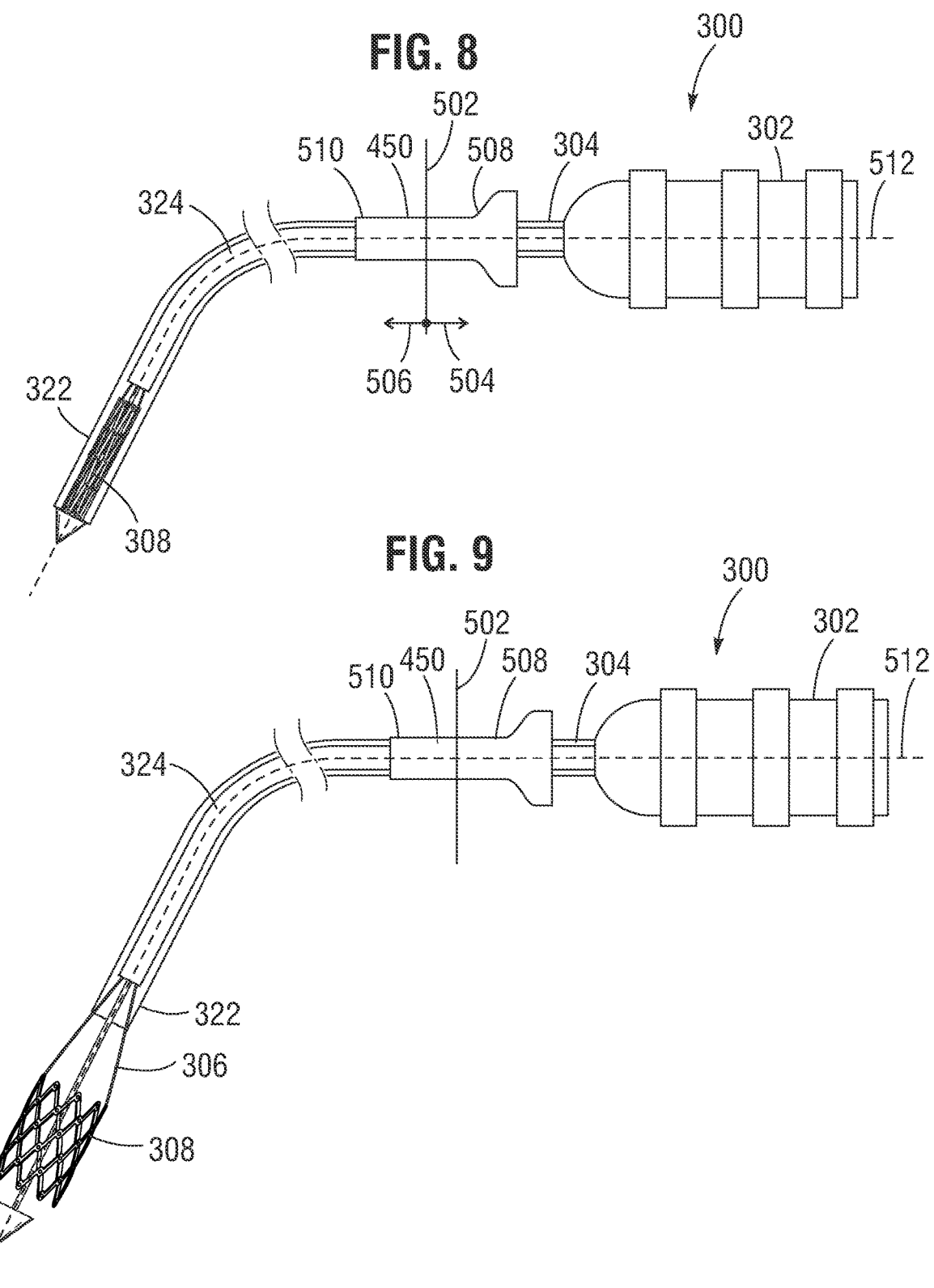
FIG. 8 is a schematic depicting advancement of a transcatheter delivery apparatus, inserted through an introducer sheath, to a target implantation site for a prosthetic medical device (e.g., prosthetic hearth valve) arranged in a radially compressed state at a distal end of the delivery apparatus and covered by a capsule of an outer shaft of the delivery apparatus.
FIG. 9 is a schematic depicting the transcatheter delivery apparatus of FIG. 8, after the capsule has been retracted to uncover the prosthetic medical device upon reaching the target implantation site.

FIGS. 8 and 9 are schematic depictions of different stages during a procedure for implanting a prosthetic medical device (e.g., a prosthetic heart valve) using a transcatheter delivery system, the transcatheter delivery system including an introducer sheath and delivery apparatus. In the embodiment shown in FIGS. 8 and 9, the introducer sheath 450 from FIG. 7 (shown in a simplified, schematic form in FIGS. 8 and 9) is inserted into a body of a patient and used for introducing the delivery apparatus 300 of FIGS. 5-7 into the patient's vasculature. Though the introducer sheath 450 and delivery apparatus 300 are depicted in FIGS. 8 and 9, in alternate embodiments, a different type of delivery apparatus and/or introducer sheath may be used for delivering the prosthetic medical device to a target implantation site.

As shown in the embodiment of FIGS. 8 and 9, the introducer sheath 450 extends through a patient point of entry 502 and into the patient's vasculature. In some embodiments, the patient point of entry 502 can be an incision in a femoral artery or femoral vein of the patient. In other embodiments, the patient point of entry 502 may be an incision in another vessel of the patient.

As shown in FIGS. 8 and 9, all components to the right of the patient point of entry 502 (e.g., in a proximal direction), as shown by arrow 504, are external to the patient, while all components to the left of the patient point of entry 502 (e.g., in a distal direction), as shown by arrow 506, are internal to the patient.

Thus, the introducer sheath 450 has a proximal portion 508 that extends from the patient point of entry 502 and outwards and a distal portion 510 that extends from the patient point of entry 502, into the patient's vasculature, and along a portion of a length of the patient's blood vessel, in route to the target implantation site. The proximal portion 508 includes the housing, such as housing 452, of the introducer sheath 450. The distal portion 510 includes the portion of the sleeve, such as sleeve 454, that is inserted into the vessel.

A delivery apparatus, such as delivery apparatus 300 (as shown in FIGS. 8 and 9), is then utilized to deliver a prosthetic medical device (e.g., prosthetic valve 308) to the target implantation site. As explained above with reference to FIGS. 5 and 6, the delivery apparatus 300 includes an outer shaft (e.g., capsule sheath) 304, an intermediate shaft (e.g., delivery system catheter containing one or more actuator assemblies for the prosthetic valve 308) 324, and a handle 302 configured to control the outer shaft 304, actuator assemblies, and expansion of the prosthetic valve 308.

The outer shaft 304 and intermediate shaft 324 extend through the introducer sheath 450 to deliver the prosthetic valve 308 to the target implantation site. As described above with reference to FIGS. 5 and 6, the outer shaft 304 includes a distal capsule 322 covering the crimped prosthetic valve 308 (as shown in FIG. 8).

Once the prosthetic valve 308 is positioned at a designated (e.g., predetermined, desired position) at the target implantation site, the capsule 322 may be retracted, along with a remainder of the outer shaft 304, in a proximal direction toward the handle 302. As explained above, the handle may be used to actuate retraction of the capsule 322 in order to expose the prosthetic valve 308 (which may partially expand once exposed). FIG. 9 shows the prosthetic valve 308 in this partially expanded state, after retraction of the capsule 322. As also explained above with reference to FIGS. 5 and 6, the handle 302 may be further utilized to fully expand the prosthetic valve 308 against the native anatomy (e.g., against the aortic annulus), and then disengage the prosthetic valve 308 from the delivery apparatus 300, to enable full retraction of the delivery apparatus 300 thereafter.

Since an outer surface of the outer shaft 304 is in contact with an inner surface of the introducer sheath 450, in the vicinity of the patient point of entry 502 and along a length of the introducer sheath 450, when the capsule 322 is retracted (proximally, in the axial direction, via actuation of the handle 302, the outer shaft 304 may rub against the inner surface of the introducer sheath 450. Thus, since the outer shaft 304 is connected to the handle 302, the handle 302 may experience undesirable movement (e.g., in the axial direction, as defined along the central longitudinal axis 512 of the delivery apparatus 300, introducer sheath 450, and patient's vessel) as a result of the outer shaft's 304 rubbing contact with the introducer sheath 450 during capsule retraction. Since the handle 302 is also connected to the intermediate shaft 324, which is carrying (e.g., attached to) the prosthetic valve 308, movement of the handle 302 may cause axial displacement of the prosthetic valve 308 from its designated position for implantation at the target implantation site. For example, unintentional movement of the handle 302 in a more proximal axial direction (e.g., further away from the patient point of entry 502, in the direction of arrow 504) may cause the prosthetic valve 308 to also move in the proximal axial direction, away from the designated position for implantation. As another example, unintentional movement of the handle 302 in a more distal axial direction (e.g., further toward the patient point of entry 502, in the direction of arrow 506) may cause the prosthetic valve 308 to also move in the distal axial direction, away from the designated position for implantation. As such, unintentional movements of the handle 302 may cause displacement of the prosthetic valve 308 away from the designated position for implantation. As a result, a physician may have to reposition to prosthetic valve 308 at the target implantation site. This may increase time and effort during the implantation procedure.

The inventors herein have realized that the patient point of entry 502 can be an actual anchor point relative to which the handle 302, shafts of the delivery apparatus 300, and the prosthetic valve 308 should retain their position in order to avoid unwanted axial movement of the prosthetic valve 308 (during capsule retraction). This may ensure that the prosthetic valve 308 is placed accurately at the target implantation site, without being displaced. Thus, by locking (e.g., fixing) the position of the handle 302 relative to the patient point of entry 502, undesirable axial movement and dispositioning of the prosthetic valve 308 from the designated position at the target implantation site during capsule 322 retraction may be reduced and/or prevented.

According to some embodiments, a locking mechanism can be configured to fix (e.g., lock), in the axial direction, the axial position of the delivery apparatus handle 302 relative to the introducer sheath and the patient point of entry 502, thereby preventing handle movements and assuring the prosthetic valve 308 retains its axial position during capsule retraction.

Figure 10:
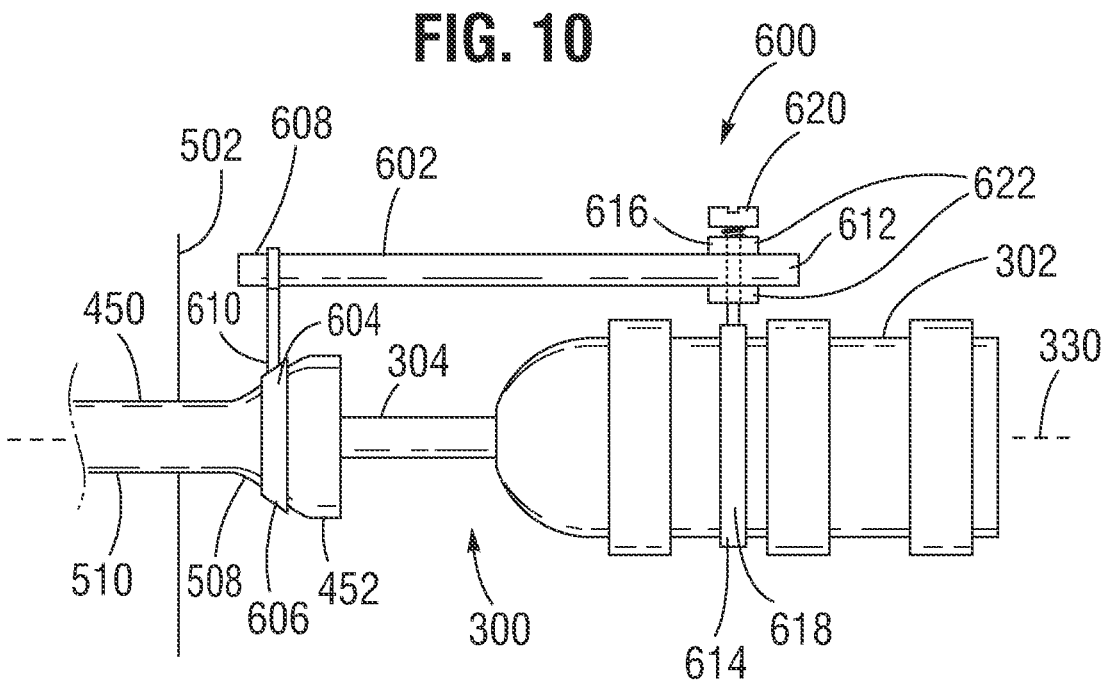
FIG. 10 is a schematic depicting a first embodiment of a locking mechanism configured to fix an axial position of a handle of a delivery apparatus relative to a patient point of entry and a proximal portion of an introducer sheath.
Figure 11:
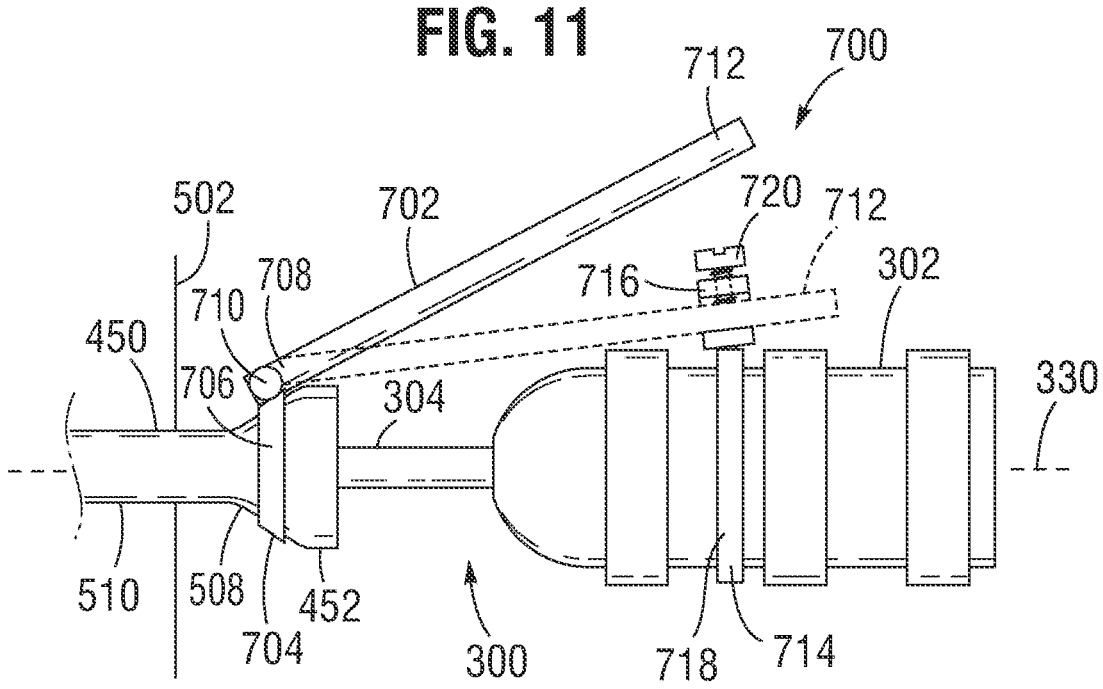
FIG. 11 is a schematic depicting a second embodiment of a locking mechanism configured to fix an axial position of a handle of a delivery apparatus relative to a patient point of entry and a proximal portion of an introducer sheath.

FIGS. 10 and 11 shows embodiments of locking mechanisms configured to fix the axial position of a handle of a delivery apparatus (e.g., handle 302 of delivery apparatus 300, as shown in FIGS. 5-11) relative to an introducer sheath and a patient point of entry 502 during a portion of a prosthetic device implantation procedure. For example, the portion of the prosthetic device implantation procedure can be during retraction of an axially moveable external sheath or capsule of the delivery apparatus to uncover and deploy the prosthetic device after reaching a desired position at the target implantation site.

Though the delivery apparatus 300 is depicted in the embodiments of FIGS. 10 and 11, in alternate embodiments, the locking mechanism of FIGS. 10 and 11 may be used to fix the axial position of a handle of an alternate delivery apparatus (e.g., an alternate delivery apparatus configured to deliver a prosthetic medical device to a target implantation site through a patient's vasculature) having an axially moveable external sheath or capsule. Further, while FIGS. 10 and 11 show the introducer sheath 450 inserted into and through the patient point of entry 502, for introducing the delivery apparatus 300 into the patient's vasculature, in alternate embodiments, an alternate sheath (e.g., having a different geometry or different components than depicted) may be used to introduce the delivery apparatus into the patient's vasculature.

Turning first to FIG. 10, a schematic depiction of a first embodiment of a locking mechanism 600 configured to fix (e.g., lock) the axial position of the handle 302 of the delivery apparatus 300 relative to an introducer sheath and the patient point of entry 502 is shown.

The locking mechanism 600 can comprise a locking arm 602 fixedly attached to a proximal portion 508 of the introducer sheath 450 and configured to be removably coupled to the handle 302. The proximal portion 508 of the introducer sheath 450 is a portion of the introducer sheath 450 arranged external to the patient (e.g., proximal to the patient point of entry 502, as shown in FIG. 10). In some embodiments, the proximal portion 508 of the introducer sheath 450 may be arranged at or adjacent to the patient point of entry 502. In some embodiments, the proximal portion 508 of the introducer sheath 450 may be or include a housing 452 of the introducer sheath 450.

In some embodiments, the locking arm is a rigid bar (with a cylindrical, square, oval, or rectangular cross-section, for example).

In the embodiment shown in FIG. 10, the locking arm 602 is fixedly attached to a first fixing member 604. The first fixing member 604 is attached to the proximal portion 508 of the introducer sheath 450. In some embodiments, the first fixing member 604 is attached to a housing 452 of the introducer sheath 450.

In some embodiments, the first fixing member 604 is removably coupled to the proximal portion 508 of the introducer sheath 450 so that the locking mechanism 600 may be removed (e.g., uncoupled) from the introducer sheath 450 at various points during an implantation procedure (e.g., removed during insertion of the introducer sheath 450 and/or delivery apparatus 300 into the patient's vasculature and/or removed after retracting the capsule to uncover the prosthetic valve at the target implantation site).

As shown in FIG. 10, a distal portion (e.g., distal or first end) 608 of the locking arm 602 is fixedly attached to the first fixing member 604. For example, in some embodiments, the distal portion 608 of the locking arm 602 may be fixedly coupled to the first fixing member 604 via a linking member 610 (e.g., such as a rod, linking arm, or clamp) that extends between the distal portion 608 of the locking arm 602 and the first fixing member 604. The linking member 610 may be configured to provide a rigid connection between the distal portion 608 of the locking arm 602 and the first fixing member 604 such that the distal portion 608 of the locking arm 602 cannot move axially relative to the first fixing member 604.

In one embodiment, as shown in FIG. 10, the first fixing member 604 is a first ring member 606. As shown in FIG. 10, the first ring member 606 may surround an outer circumference of the proximal portion 508 of the introducer sheath 450 (e.g., the housing 452). In this way, the first ring member 606 may encircle the proximal portion 508 of the introducer sheath 450.

In alternate embodiments, the first fixing member 604 may be alternate type of fixing member configured to rigidly couple the distal portion 608 of the locking arm 602 to the proximal portion 508 of the introducer sheath 450. For example, in alternate embodiments, the first fixing member 604 may be a mechanical hook, clamp, or the like.

In some embodiments, the first linking member 610 may not be present and the first fixing member 604 may extend between and couple to each of the proximal portion 508 of the introducer sheath 450 and the distal portion 608 of the locking arm 602 in order to rigidly fix the locking arm 602 to the introducer sheath 450.

In this way, the first fixing member 604 may be configured to prevent relative movement (in at least the axial direction, arranged along the central longitudinal axis 330 of the delivery apparatus) between the locking arm 602 and the introducer sheath 450.

According to some embodiments (as shown in FIG. 10), the introducer sheath 450 is provided with the distal portion 608 of the locking arm 602 attached thereto (e.g., fixedly attached). According to other embodiments, the distal portion 608 of the locking arm 602 is removably coupled to the introducer sheath 450, such that the distal portion 608 of the locking arm 602 may be attached to the proximal portion 508 of the introducer sheath 450 prior to initiating capsule and outer shaft 304 retraction. For example, the locking arm 602 may be attached to the introducer sheath 450 via the first fixing member 604 which may be a removable snap-fit clamp (or another type of removable member) instead of an affixed first ring member.

As shown in FIG. 10, a proximal portion 612 of the locking arm 602 is removably coupled to the handle 302. For example, the proximal portion 612 of the locking arm 602 is removably coupled to the handle 302 via a clamping mechanism 616 and a second fixing member 614 that is configured to be coupled to the handle 302 and the clamping mechanism 616.

As shown in FIG. 10, the second fixing member 614 is attached to the handle 302. In some embodiments, the second fixing member 614 is removably coupled to the handle 302 so that the locking mechanism 600 may be removed (e.g., uncoupled) from the handle 302 at various points during an implantation procedure (e.g., removed during insertion of the delivery apparatus 300 into the patient's vasculature and/or removed after retracting the capsule to uncover the prosthetic valve at the target implantation site), as desired by the user.

As shown in FIG. 10, the proximal portion (e.g., proximal or second end) 612 of the locking arm 602 is removably (e.g., not permanently) attached to the second fixing member 614. In some embodiments, the proximal portion 612 of the locking arm 602 may be removably coupled to the second fixing member 614 via the clamping mechanism 616 which is attached to the second fixing member 614.

In some embodiments, the clamping mechanism 616 may include a first end that is fixedly attached and/or part of (e.g., integrated with) the second fixing member 614 and a second end that is configured to removably couple with the proximal portion 612 of the locking arm 602.

In some embodiments, the clamping mechanism 616 can be a screw-clamp. The screw-clamp can include two opposing jaws where a space between the jaws is adjustable via a screw mechanism of the screw-clamp and wherein the jaws are adapted to secure an object therebetween. In some embodiments, the screw-clamp can include a C-clamp, F-clamp, and the like.

In other embodiments, the clamping mechanism 616 can be a snap-clamp that may pivot about a point attached to the second fixing member 614 and be configured to snap around the locking arm 602 via a press-fit connection.

As introduced above, the clamping mechanism 616 can be attached to the handle 302 via the second fixing member 614. In one embodiment, as shown in FIG. 10, the second fixing member 614 is a second ring member 618. As shown in FIG. 10, the second ring member 618 can surround an outer circumference of a portion of the handle 302. In this way, the second ring member 618 may encircle the handle 302.

In alternate embodiments, the second fixing member 614 may be an alternate type of fixing member configured to rigidly couple the handle 302 to the clamping mechanism 616 such that the handle 302 and clamping mechanism 616 are fixed, in the axial direction, relative to one another. For example, in alternate embodiments, the second fixing member 614 may be a mechanical hook, clamp, or the like.

In the embodiment shown in FIG. 10, the proximal portion 612 of the locking arm 602 may be inserted into an opening or a central bore of the clamping mechanism 616 (e.g., between the two opposing jaws 622). For example, the locking arm 602 may be configured so slide back and forth (proximally and distally), in the axial direction, when the clamping mechanism 616 is in an unlocked configuration (e.g., where the distance between the opposing jaws 622 of the clamping mechanism 616 is greater than a diameter or width (e.g., in a direction perpendicular to the axial direction) of the locking arm 602).

In use, during an implantation procedure using the delivery apparatus 300, the shafts and internal components of the delivery apparatus 300 (e.g., the outer shaft 304 and the intermediate shaft) are inserted through the introducer sheath 450 to position the prosthetic valve (e.g., prosthetic valve 308, as shown in FIGS. 8 and 9) at the target implantation site. During the navigation of the prosthetic valve to the target implantation site via the delivery apparatus 300, the handle 302 and the delivery apparatus components attached thereto may move freely (e.g., in the axial direction) relative to the introducer sheath 450. Once the prosthetic valve is positioned at the target implantation site, and prior to capsule retraction (e.g., retraction of outer shaft 304), the locking arm 602, which is affixed to the proximal portion 508 of the introducer sheath 450, as described above, extends through a central opening (e.g., between the opposing jaw 622) of the clamping mechanism 616. The clamping mechanism 616 may then be adjusted to secure (e.g., lock) the locking arm (at the proximal portion 612) within the clamping mechanism 616, thereby rigidly fixing the locking arm 602 to the handle 302. For example, in the embodiment where the clamping mechanism 616 is a screw-clamp, a screw 620 can be screwed in a direction so as to clamp the proximal portion 612 of the locking arm 602 within jaws 622 of the screw-clamp, thereby immobilizing axial movement of the locking arm 602 relative to the handle 302.

After adjusting the clamping mechanism 616 into the locked position with the locking arm 602, the locking arm 602 is rigidly attached to both the introducer sheath 450 (proximate to the patient point of entry 502) and the handle 302. As a result, the handle 302 cannot move axially relative to the introducer sheath 450 (referred to herein as the locked position or configuration). Said another way, in this configuration, the axial position of the handle 302 is fixed relative to the introducer sheath 450.

In this locked configuration, the outer shaft 304 and the capsule covering the prosthetic valve can be retracted, proximally along the axial direction, without axial movement of the handle 302 (e.g., due to the outer shaft rubbing against the introducer sheath). Since the prosthetic valve and the intermediate shaft of the delivery apparatus 300 are axially immovable relative to the handle 302 during the phase of capsule (outer shaft 304) retraction, due to fixing the axial position of the handle 302 relative to the introducer sheath 450 via the locking mechanism 600, axial displacement of the prosthetic valve (e.g., away from the desired location at the target implantation site) can be avoided.

Once the outer shaft 304 is retracted and the prosthetic valve is uncovered such that it may be expanded and implanted at the target implantation site, the locking mechanism 600 may be adjusted into an unlocked position or configuration where the locking arm 602 is not locked (e.g., rigidly coupled in the axial direction) with the clamping mechanism 616, and thus, the handle 302. As a result, the handle 302 is free to move axially relative to the introducer sheath 450 and the patient point of entry 502. Said another way, in the unlocked configuration, the handle 302 and introducer sheath 450 are axially movable relative to one another.

In the embodiment where the clamping mechanism 616 is a screw-clamp, the screw 620 may be adjusted (e.g., rotated) to release the locking arm 602 from being held between the jaws 622 of the clamping mechanism 616.

In one embodiment, the clamping mechanism 616 may be adjusted into the unlocked position or configuration, allowing axial movement of the handle 302 relative to the introducer sheath 450, to enable full retraction (e.g., removal) of the delivery apparatus 300 from the patient's body, after valve implantation.

In another embodiment, the clamping mechanism 616 may be adjusted into the unlocked position during the implantation procedure, when axial repositioning of the prosthetic valve is desired (e.g., as determined by a user to move the prosthetic valve to the desired location for implantation).

According to some embodiments, the handle 302 is provided with the clamping mechanism 616 attached thereto. According to other embodiments, the clamping mechanism 616 is removably coupleable to the handle 302, such that the clamping mechanism 616 may be attached thereto prior to initiating capsule and outer shaft 304 retraction. For example, the clamping mechanism 616 may be removably attachable via the second fixing member 614 which may be a removable snap-fit clamp, a snap-fit pin, a screwable connector, or the like, instead of the affixed second ring member 618.

In this way, the locking mechanism 600 provides a mechanism for locking a handle of a delivery apparatus at a fixed distance, in the axial direction. relative to an introducer sheath, thereby preventing undesirable axial displacement of the prosthetic valve which is coupled to the delivery apparatus, during capsule retraction, without requiring any structural modifications to either the delivery apparatus or the introducer sheath (e.g., since the components of the locking mechanism 600 can be removably attached to both the delivery apparatus and the introducer sheath).

FIG. 11 shows a schematic depiction of a second embodiment of a locking mechanism 700 configured to fix the axial position of the handle 302 of the delivery apparatus 300 relative to the patient point of entry 502.

The locking mechanism 700 can comprise a locking arm 702 fixedly attached to a proximal portion 508 of the introducer sheath 450 and configured to be removably coupled to the handle 302. The locking arm 702 can be similar to the locking arm 602 shown in FIG. 10, as described above.

In the embodiment shown in FIG. 11, and similar to the embodiment of FIG. 10, the locking arm 702 is fixedly attached to a first fixing member 704 that is attached to the proximal portion 508 of the introducer sheath 450. In some embodiments, the first fixing member 704 is attached to a housing 452 of the introducer sheath 450. As described above with reference to FIG. 10, in some embodiments, the first fixing member 704 may be removably coupled (e.g., attached) to the proximal portion 508 of the introducer sheath 450.

Instead of being rigidly coupled to the first fixing member (as shown in the locking mechanism embodiment of FIG. 10), a distal portion (e.g., end) 708 of the locking arm 702 is pivotably coupled (e.g., attached) to the first fixing member 704 via a pivot mechanism 710. As a result, the locking arm 702 is able to pivot around its distal end 708.

In some embodiments, the pivot mechanism 710 may be a hinge joint, ball joint, or the like.

In some embodiments, as shown in FIG. 11, the first fixing member 704 is a first ring member 706. As shown in FIG. 11, the first ring member 706 may surround an outer circumference of the proximal portion 508 of the introducer sheath 450 (e.g., the housing 452).

In alternate embodiments, the first fixing member 704 may be alternate type of fixing member configured to couple the proximal portion 508 of the introducer sheath 450 to the pivot mechanism 710. For example, in alternate embodiments, the first fixing member 704 may be a mechanical hook, clamp, or the like, fixedly attached to the pivot mechanism 710.

In still other embodiments, the locking arm 702 can be pivotably attached directly to the proximal portion 508 of the introducer sheath 450 (e.g., directly to the housing 452), without a first fixing member 704. For example, the pivot mechanism 710 may be directly coupled to the housing 452 of the introducer sheath 450.

As shown in FIG. 11, and similar to the embodiment of FIG. 10, a proximal portion (e.g., end) 712 of the locking arm 702 is removably coupled to the handle 302. For example, the proximal portion 712 of the locking arm 702 can be removably coupled to the handle 302 via a clamping mechanism 716 and a second fixing member 714 that is configured to be coupled to the handle 302 and the clamping mechanism 716.

As shown in FIG. 11, the second fixing member 714 is attached to the handle. In some embodiments, the second fixing member 714 is removably coupled to the handle 302 so that the locking mechanism 700 may be removed (e.g., uncoupled) from the handle 302 at various points during an implantation procedure (e.g., removed during insertion of the delivery apparatus 300 into the patient's vasculature and/or removed after retracting the capsule to uncover the prosthetic valve at the target implantation site), as desired by the user.

In one embodiment, as shown in FIG. 11, the second fixing member 714 is a second ring member 718. As shown in FIG. 11, the second ring member 718 can surround an outer circumference of a portion of the handle 302. In this way, the second ring member 718 may encircle the handle 302.

In alternate embodiments, the second fixing member 714 may be an alternate type of fixing member configured to rigidly couple the handle 302 to the clamping mechanism 716 such that the handle 302 and clamping mechanism 716 are fixed, in the axial direction, relative to one another. For example, in alternate embodiments, the second fixing member 714 may be a mechanical hook, clamp, or the like.

As shown in FIG. 11, the proximal portion 712 of the locking arm 702 is removably (e.g., not permanently) attached to the second fixing member 714. In some embodiments, the proximal portion 712 of the locking arm 702 may be removably coupled to the second fixing member 714 via the clamping mechanism 716 which is attached to the second fixing member 714.

In some embodiments, the clamping mechanism 716 may include a first end that is fixedly attached and/or part of the second fixing member 714 and a second end that is configured to removably couple with the proximal portion 712 of the locking arm 702.

In some embodiments, the clamping mechanism 716 is a screw-clamp. In some embodiments, the screw-clamp can include a C-clamp, F-clamp, and the like.

In some embodiments the screw-clamp can be formed as a partially formed ring having a side opening enabling the proximal portion 712 of the locking arm 702 to enter therethrough into its central bore (as shown by the dashed locking arm 702 in FIG. 11). Thus, once it is desired to lock the axial position of the handle 302 relative to the introducer sheath 450, the proximal portion 712 of the locking arm 702 may be moved from exterior to the central bore of the clamping mechanism 716 (as shown by the solid-line locking arm 702 in FIG. 11) into the central bore of the clamping mechanism 716, through the side-opening (as shown by the dashed-line locking arm 702 in FIG. 11). A screw 720 of the clamping mechanism 716 may then be adjusted (e.g., rotated) such that it presses against the proximal portion 712 of the locking arm 702 and locks it in place. In alternate embodiments, the clamping mechanism 716 may be the same or similar to the clamping mechanism 616 of FIG. 10.

In use, the locking mechanism 700 may function similarly to that of the locking mechanism 600 of FIG. 10, as described above. However, due to the inclusion of the pivot mechanism 710, the locking mechanism 700 may provide a higher degree of flexibility in switching between a locking arm 702 released or unlocked state or configuration (solid lines in FIG. 11) and a locking arm 702 locked state or configuration (dashed lines in FIG. 11), at a desired distance between the handle 302 and the patient point of entry 502 (or alternatively, the region of the connection between the first fixing member 704 and the introducer sheath 450).

In this way, the locking mechanism 700 provides a mechanism for locking a handle of a delivery apparatus at a fixed distance, in the axial direction. relative to an introducer sheath, thereby preventing undesirable axial displacement of the prosthetic valve which is coupled to the delivery apparatus, during capsule retraction, without requiring any structural modifications to either the delivery apparatus or the introducer sheath (e.g., since the components of the locking mechanism 700 can be removably attached to both the delivery apparatus and the introducer sheath).

In all the embodiments of the locking mechanism shown in FIGS. 10 and 11, the fixed distance between the handle 302 and the proximal portion 508 of the introducer sheath 450 may be adjustable based on patient size, delivery apparatus configuration, and/or user preference. For example, the locking arm of the locking mechanism may slide (as shown in FIG. 10) or pivot (as shown in FIG. 11)

into and out of the clamping mechanism (e.g., into and out of engagement with the clamping mechanism) and be removably coupled to the clamping mechanism at various points along the distal portion of the locking arm. As a result, a same locking mechanism may be used in a variety of patients, with different delivery systems or apparatuses, and for different users.

FIG. 12 shows a flow chart of a method 800 for locking (e.g., fixing) a handle of a delivery apparatus, the delivery apparatus configured to deliver a prosthetic medical device to a target implantation site in a patient, at a fixed distance, in an axial direction, relative to an introducer sheath used to introduce the delivery apparatus into the vasculature of the patient. In some embodiments, the handle of the delivery apparatus may be locked at a fixed distance, in the axial direction (relative to a central longitudinal axis of the delivery apparatus), from a patient point of entry (and/or the introducer sheath) such that the handle is held in place, axially, relative to the patient point of entry during a portion of the implantation procedure.

In some embodiments, the delivery apparatus may be part of a transcatheter delivery system including an introducer sheath, the delivery apparatus configured to deliver a prosthetic medical device (e.g., a prosthetic heart valve) to the target implantation site within the patient, such as the delivery apparatus 300 shown in FIGS. 5-11.

In some embodiments, the introducer sheath may be the introducer sheath 450 shown in FIGS. 7-11.

Method 800 begins at 802 by inserting the introducer sheath into a patient's vasculature, via a patient point of entry so that a proximal portion of the introducer sheath is arranged external to the point of entry into the patient's vasculature and a distal portion of the introducer sheath is arranged internal to the point of entry, and toward a target implantation site for a prosthetic device.

At 804, method 800 includes inserting an outer shaft of the delivery apparatus (and all of the components of the delivery apparatus arranged internal to the outer shaft) into the introducer sheath and advancing the outer shaft through the introducer sheath and the patient's vasculature to the target implantation site, where a distal end portion of the outer shaft forms a capsule enclosing a radially compressed prosthetic device (e.g., valve) therein. In one example, the delivery apparatus may be the delivery apparatus 300 shown in FIGS. 5-11 and the prosthetic device may be a prosthetic valve, such as one of the prosthetic valves shown in FIGS. 1-6, 8, and 9. For example, the distal end portion of the outer shaft containing the radially compressed prosthetic valve may be advanced to the target implantation site via a handle of the delivery apparatus, the handle arranged external to the patient (e.g., proximally relative to the patient point of entry).

Continuing to 806, method 800 includes, after reaching the target implantation site (e.g., after the radially compressed prosthetic valve reaches the desired location for implantation at the target implantation site), locking an axial position of the handle of the delivery apparatus relative to the proximal portion of the introducer sheath. Said another way, the method at 806 can include locking the handle at a fixed distance, in an axial direction arranged along a central longitudinal axis of the delivery apparatus, from the introducer sheath.

In some embodiments, the method at 806 includes locking the axial position of the handle relative to the proximal portion of the introducer sheath via a locking mechanism configured to couple to each of the handle and the proximal portion of the introducer sheath. As an example, the locking mechanism may be the locking mechanism 600 shown in FIG. 10 and/or the locking mechanism 700 shown in FIG. 11, as described above.

The locking mechanism can comprise a locking arm configured to couple to each of the handle and the proximal portion of the introducer sheath. When the locking arm is coupled to both the introducer sheath and the handle, these parts are rigidly connected to one another and the distance between the handle and the proximal portion of the introducer sheath may be fixed such that the handle cannot move, in the axial direction, relative to the introducer sheath.

In some embodiments, locking the axial position of the handle relative to the proximal portion of the introducer sheath at 806 includes coupling a proximal portion of the locking arm of the locking mechanism to the handle while a distal portion of the locking arm is fixed to the proximal portion of the introducer sheath. For example, at 806, the method may include sliding or pivoting the proximal portion (e.g., end) of the locking arm into an opening of a clamping mechanism attached to the handle and then adjusting the clamping mechanism to clamp (e.g., rigidly hold or couple to) the proximal portion of the locking arm. Since a distal portion of the locking arm can be rigidly coupled to the proximal portion of the introducer sheath, clamping the proximal portion of the locking arm via the clamping mechanism causes the handle and proximal portion of the introducer sheath to be rigidly connected to one another, in the axial direction, via the locking arm. As a result, their relative axial positions are fixed and the handle may not move in the axial direction relative to the patient point of entry.

In some embodiments, the method at 806 may further include, prior to locking the axial position of the handle via the locking mechanism, attaching the locking mechanism to the proximal portion of the introducer sheath and the handle. For example, a first fixing member of the locking mechanism, the first fixing member attached to the distal portion of the locking arm, may be attached to the proximal portion of the introducer sheath and a second fixing member of the locking mechanism, the second fixing member attached to the clamping mechanism, may be attached to the handle. The clamping mechanism may then be adjusted to rigidly couple to the proximal portion of the locking arm, thereby locking the axial position of the handle relative to the proximal portion of the introducer sheath.

After locking the axial position of the handle relative to the introducer sheath, method 800 continues to 808 to retract the capsule (and the outer shaft) of the delivery apparatus to uncover the prosthetic valve. Since the axial position of the handle is locked relative to the introducer sheath, and the prosthetic valve is connected to the handle via components of the delivery apparatus, the method at 808 includes maintaining the prosthetic valve at a desired axial position at the target implantation site during retraction of the outer shaft to uncover the prosthetic valve. As a result, repositioning of the prosthetic valve due to unwanted movement of the handle during capsule retraction may not be necessary, thereby saving a user time and effort during the implantation procedure.

The method may further include implanting the prosthetic valve at the target implantation site by radially expanding the prosthetic valve to its fully expanded state via the delivery apparatus and then detaching the prosthetic valve from the delivery apparatus.

After retracting the capsule and/or implanting the prosthetic valve at the target implantation site, method 800 continues to 810 to unlock the axial position of the handle relative to the introducer sheath and retract the delivery apparatus from the target implantation site and the patient. In some embodiments, unlocking the axial position of the handle relative to the introducer sheath at 810 may include adjusting the clamping mechanism of the locking mechanism to release the proximal end of the locking arm so that the handle may move axially relative to the introducer sheath.

In some embodiments, the method at 810 may include uncoupling the locking mechanism from both the handle and the introducer sheath prior to retracting the delivery apparatus from the target implantation site. For example, the locking arm may be configured to couple to the proximal portion of the introducer sheath via the first fixing member of the locking mechanism and couple to the handle via the second fixing member of the locking mechanism. Each of the first fixing member and the second fixing member can be configured to removably couple to the introducer sheath and the handle, respectively. Thus, in some embodiments, uncoupling the locking mechanism from both the handle and the introducer sheath may include detaching the first fixing member from the introducer sheath and detaching the second fixing member from the handle.

In this way, a locking mechanism for a transcatheter delivery system may be configured to lock an axial position, in a direction of a central longitudinal axis of the transcatheter delivery system, of a handle of a delivery apparatus of the transcatheter delivery system relative to an axial position of a patient point of entry and/or a proximal portion of an introducer sheath of the transcatheter delivery system (the proximal portion arranged exterior to the patient point of entry). As such, in this locked configuration, the handle will not move axially relative to the proximal portion of the introducer sheath (e.g., an axial distance between the handle and the proximal portion of the introducer sheath is fixed). By locking the axial position of the handle of the delivery apparatus relative to the proximal portion of the introducer sheath and/or the patient point of entry during capsule retraction (e.g., retracting the capsule covering the radially compressed prosthetic valve at a distal end of the delivery apparatus), the handle and the prosthetic valve (since it is attached to the handle via one or more shafts/catheters of the delivery apparatus) maintain their axial positions (as desired and set by a user). Thus, the prosthetic valve may not experience unwanted axial dispositioning during capsule retraction and repositioning of the prosthetic valve following capsule retraction may not be necessary, thereby saving the user time and effort during the implantation procedure.

Additionally, the locking mechanisms described herein do not require any structural modifications to either the delivery apparatus or the introducer sheath since the components of the locking mechanism may be removably coupled to each of the delivery apparatus (at the handle) and the introducer sheath (at the proximal portion). This may reduce component costs and allow for increased flexibility in use of the locking mechanism. For example, the locking mechanism may only be attached during desired portions of the implantation procedure, such as during capsule retraction. Further, by having a locking arm that is removably coupled to at least one of the handle and the introducer sheath (e.g., via a clamping mechanism), the locking mechanism may be adapted for use in patients of varying sizes and for users with different preferences.

ADDITIONAL EXAMPLES OF THE DISCLOSED TECHNOLOGY

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A locking mechanism for a transcatheter delivery system, comprising: a first fixing member configured to be coupled to an introducer sheath of the transcatheter delivery system, the introducer sheath configured to receive a portion of a delivery apparatus of the transcatheter delivery system therein; a second fixing member configured to be coupled to a handle of the delivery apparatus; and a locking arm configured to be removably coupled at a first end to one of the first fixing member and the second fixing member and fixedly or removably coupled at a second end to another one of the first fixing member and the second fixing member, wherein the locking arm is moveable between a first position where an axial position, relative to a central longitudinal axis of the transcatheter delivery system, of the second fixing member is not fixed relative to the first fixing member via the locking arm and a second position where the axial position of the second fixing member is fixed relative to the first fixing member via the locking arm.

Example 2. The locking mechanism of any example herein, particularly example 1, wherein the first fixing member is configured to be coupled to the introducer sheath, proximate to a patient point of entry at which the introducer sheath enters a vessel of a patient from outside of the patient.

Example 3. The locking mechanism of any example herein, particularly any one of examples 1-2, wherein in the second position the locking arm is rigidly coupled to each of the first fixing member and the second fixing member and the handle is locked at a fixed distance from the introducer sheath via the locking arm.

Example 4. The locking mechanism of any example herein, particularly any one of examples 1-3, wherein in the first position the locking arm is rigidly coupled to only one of the first fixing member and the second fixing member and the handle is not locked at a fixed distance from the introducer sheath via the locking arm.

Example 5. The locking mechanism of any example herein, particularly any one of examples 1-4, wherein the locking arm is removably coupled to one of the first fixing member and the second fixing member via a clamping mechanism attached to the one of the first fixing member and the second fixing member.

Example 6. The locking mechanism of any example herein, particularly example 5, wherein the clamping mechanism is a screw-clamp attached to the one of the first fixing member and the second fixing member.

Example 7. The locking mechanism of any example herein, particularly example 5, wherein the clamping mechanism is configured to receive and rigidly couple to the first end of the locking arm in the second position.

Example 8. The locking mechanism of any example herein, particularly any one of examples 5-7, wherein the locking arm is fixedly coupled to the another one of the first fixing member and the second fixing member.

Example 9. The locking mechanism of any example herein, particularly example 8, wherein the locking arm is fixedly coupled to the another one of the first fixing member and the second fixing member via a pivot mechanism and wherein the locking arm is configured to pivot about the pivot mechanism to move between the first position and the second position.

Example 10. The locking mechanism of any example herein, particularly any one of examples 1-9, wherein the first fixing member is a ring configured to be removably coupled to and around a proximal portion of the introducer sheath.

Example 11. The locking mechanism of any example herein, particularly any one of examples 1-10, wherein the second fixing member is a ring configured to be removably coupled to and around the handle of the delivery apparatus.

Example 12. A method, comprising: advancing a portion of a transcatheter delivery apparatus through an introducer sheath inserted into a vessel of a patient and to a target implantation site for a prosthetic valve, wherein a distal end portion of an outer shaft of the delivery apparatus forms a capsule enclosing the prosthetic valve in a radially compressed state and wherein the introducer sheath includes a proximal portion arranged external to a point of entry into the vessel of the patient and a distal portion arranged internal to the point of entry; and after the distal end portion of the outer shaft of the delivery apparatus reaches the target implantation site and prior to retracting the capsule to uncover the prosthetic valve, locking an axial position of a handle of the delivery apparatus relative to the proximal portion of the introducer sheath via a locking mechanism configured to couple to each of the handle and the proximal portion of the introducer sheath, wherein the handle is arranged external to the point of entry.

Example 13. The method of any example herein, particularly example 12, further comprising, after locking the axial position of the handle relative to the proximal portion of the introducer sheath: retracting the outer shaft, including the capsule, to uncover the prosthetic valve; and implanting the prosthetic valve at the target implantation site.

Example 14. The method of any example herein, particularly example 13, further comprising, after retracting the outer shaft, unlocking the axial position of the handle relative to the proximal portion of the introducer sheath.

Example 15. The method of any example herein, particularly any one of examples 12-14, wherein locking the axial position of the handle relative to the proximal portion of the introducer sheath includes maintaining the handle at a fixed axial distance from the proximal portion of the introducer sheath.

Example 16. The method of any example herein, particularly any one of examples 12-15, wherein locking the axial position of the handle relative to the proximal portion of the introducer sheath further comprises maintaining the prosthetic valve at a desired axial position at the target implantation site during retraction of the outer shaft to uncover the prosthetic valve.

Example 17. The method of any example herein, particularly any one of examples 12-16, wherein locking the axial position of the handle relative to the proximal portion of the introducer sheath includes coupling a proximal portion of a locking arm of the locking mechanism to the handle of the delivery apparatus and wherein a distal portion of the locking arm is attached to the proximal portion of the introducer sheath.

Example 18. An assembly comprising: an introducer sheath; a delivery apparatus including a handle and an outer shaft that is coupled to and movable, in an axial direction arranged along a central longitudinal axis of the delivery apparatus, relative to the handle; and a locking mechanism, comprising: a locking arm having a first end portion fixedly coupled to a proximal portion of the introducer sheath and a second end portion configured to be removably coupled to the handle, wherein the locking arm is movable between an unlocked, first position where the second end portion is not rigidly coupled to the handle and the handle is able to move, in the axial direction, relative to the proximal portion of the introducer sheath and a locked, second position where the second end portion is rigidly coupled to the handle and the handle is maintained at a fixed distance, in the axial direction, from the proximal portion of the introducer sheath.

Example 19. The assembly of any example herein, particularly example 18, wherein the second end portion of the locking arm is configured to be removably coupled to the handle via a clamping mechanism of the locking mechanism, the clamping mechanism attached to the handle.

Example 20. The assembly of any example herein, particularly example 19, wherein the clamping mechanism is removably coupled to the handle.

Example 21. The assembly of any example herein, particularly example 19, wherein the clamping mechanism is a screw-clamp comprising a central bore adapted to receive the second end portion of the locking arm and wherein in the locked, second position the screw-clamp is rigidly coupled to the second end portion of the locking arm within the central bore.

Example 22. The assembly of any example herein, particularly any one of examples 19-21, wherein the locking mechanism further comprises a first fixing member removably coupled to the proximal portion of the introducer sheath and a second fixing member removably coupled to the handle, wherein the first fixing member is rigidly coupled to the first end portion of the locking arm, and wherein the second fixing member is coupled to or part of the clamping mechanism.

Example 23. The assembly of any example herein, particularly any one of examples 18-22, wherein the first end portion of the locking arm is pivotably coupled to the proximal portion of the introducer sheath via a pivot mechanism.

Example 24. The assembly of any example herein, particularly any one of examples 18-23, wherein the proximal portion of the introducer sheath is configured to be arranged proximate to a point of entry into a vessel of a patient into which the introducer sheath is inserted.

Example 25. The assembly of any example herein, particularly any one of examples 18-24, wherein the delivery apparatus is adapted to carry a prosthetic valve in a radially compressed state within a distal end of the outer shaft.

Example 26. An assembly comprising: an introducer sheath; a delivery apparatus including a handle and an outer shaft that is coupled to and movable, in an axial direction arranged along a central longitudinal axis of the delivery apparatus, relative to the handle; and a locking mechanism configured to lock an axial position of the handle of the delivery apparatus relative to a proximal portion of the introducer sheath.

Example 27. The assembly of any example herein, particularly example 26, wherein the locking mechanism is configured to couple to each of the handle and the proximal portion of the introducer sheath.

Example 28. The assembly of any example herein, particularly any one of examples 26-27, wherein the locking mechanism is configured to move between an unlocked configuration and a locked configuration, wherein in the unlocked configuration the handle and introducer sheath are axially moveable relative to one another and in the locked configuration the handle and introducer sheath are fixed and not axially movable relative to one another.

Example 29. The assembly of any example herein, particularly example 28, wherein in the unlocked configuration the locking mechanism is uncoupled from at least one of the handle and the introducer sheath.

Example 30. The assembly of any example herein, particularly any one of examples 28-29, wherein in the locked configuration the locking mechanism is coupled to each of the handle and the introducer sheath.

Example 31. The assembly of any example herein, particularly any one of examples 26-30, wherein the locking mechanism comprises a locking arm that is fixedly coupled to the introducer sheath and removably coupled to the handle.

Example 32. The assembly of any example herein, particularly any one of examples 26-30, wherein the locking mechanism comprises a locking arm that is fixedly coupled to the handle and removably coupled to the handle.

Example 33. The assembly of any example herein, particularly any one of examples 26-30, wherein the locking mechanism comprises a locking arm that is removably coupled to each of the handle and the introducer sheath.

Example 34. The assembly of any example herein, particularly any one of examples 26-33, wherein the locking mechanism comprises a locking arm and a clamping mechanism attached to one of the handle and the introducer sheath.

Example 35. The assembly of any example herein, particularly examples 34, wherein the locking arm is configured to be removably coupled to the clamping mechanism at a first end of the locking arm.

Example 36. The assembly of any example herein, particularly example 35, wherein a second end of the locking arm is fixed to another one of the handle and the introducer sheath.

Example 37. The assembly of any example herein, particularly any one of examples 35-36, wherein the locking arm is configured to pivot into and out of engagement with the clamping mechanism.

Example 38. The assembly of any example herein, particularly any one of examples 35-36, wherein the locking arm is configured to slide into and out of engagement with the clamping mechanism.

Example 39. The assembly of any example herein, particularly any one of examples 34-38, wherein the clamping mechanism is a screw-clamp.

Example 40. The assembly of any example herein, particularly any one of examples 26-39, wherein the locking mechanism is configured to lock and hold the handle at a fixed distance from the introducer sheath.

Example 41. The assembly of any example herein, particularly example 40, wherein the fixed distance is adjustable.

Example 42. A method comprising: adjusting a locking mechanism for a transcatheter delivery system between an unlocked configuration where an axial position, relative to a central longitudinal axis of the transcatheter delivery system, of a handle of a delivery apparatus of the transcatheter delivery system is fixed relative to an introducer sheath of the transcatheter delivery system and a locked configuration where the axial position of the handle is not fixed relative to the introducer sheath.

Example 43. The method of any example herein, particularly example 42, wherein adjusting the locking mechanism includes coupling a locking arm of the locking mechanism to each of the handle and the introducer sheath to adjust the locking mechanism into the locked configuration.

Example 44. The method of any example herein, particularly any one of examples 42-43, wherein adjusting the locking mechanism includes uncoupling a locking arm of the locking mechanism from the handle to adjust the locking mechanism from the locked configuration to the unlocked configuration.

Example 45. The method of any example herein, particularly any one of examples 42-43, wherein adjusting the locking mechanism includes uncoupling a locking arm of the locking mechanism from the introducer sheath to adjust the locking mechanism from the locked configuration to the unlocked configuration.

Example 46. The method of any example herein, particularly any one of examples 42-43, wherein adjusting the locking mechanism includes pivoting a locking arm of the locking mechanism into engagement with a clamping mechanism of the locking mechanism that is fixed to one of the handle and the introducer sheath, the locking arm fixed to another one of the handle and the introducer sheath, to adjust the locking mechanism from the unlocked configuration to the locked configuration.

Example 47. The method of any example herein, particularly any one of examples 42-43, wherein adjusting the locking mechanism includes sliding a locking arm of the locking mechanism into engagement with a clamping mechanism of the locking mechanism that is fixed to one of the handle and the introducer sheath, the locking arm fixed to another one of the handle and the introducer sheath, to adjust the locking mechanism from the unlocked configuration to the locked configuration.

Example 48. The method of any example herein, particularly any one of examples 42-47, wherein the introducer sheath is configured to receive a portion of the delivery apparatus, the portion distal to the handle.

Example 49. The method of any example herein, particularly any one of examples 42-48, wherein the delivery apparatus includes an outer shaft extending distally from the handle and wherein a distal end portion of the outer shaft of the delivery apparatus forms a capsule enclosing a prosthetic valve in a radially compressed state.

Example 50. The method of any example herein, particularly any one of examples 42-49, wherein the locking mechanism comprises a first fixing member configured to be coupled to the introducer sheath, a second fixing member configured to be coupled to the handle, and a locking arm configured to be removably coupled at a first end to one of the first fixing member and the second fixing member and fixedly or removably coupled at a second end to another one of the first fixing member and the second fixing member.

In view of the many possible embodiments to which the principles of the disclosed technology may be applied, it should be recognized that the illustrated embodiments are only examples of the disclosed technology and should not be taken as limiting the scope of the claimed subject matter. Rather, the scope of the claimed subject matter is defined by the following claims and their equivalents.

We claim:

1. A locking mechanism for a transcatheter delivery system, comprising:
a first fixing member configured to be coupled to an introducer sheath of the transcatheter delivery system, the introducer sheath configured to receive a portion of a delivery apparatus of the transcatheter delivery system therein;
a second fixing member configured to be coupled to a handle of the delivery apparatus; and
a locking arm configured to be removably coupled at a first end to one of the first fixing member and the second fixing member and permanently coupled at a second end to another one of the first fixing member and the second fixing member via a pivot mechanism, wherein the locking arm is moveable between a first position where an axial position, relative to a central longitudinal axis of the transcatheter delivery system, of the second fixing member is not fixed relative to the first fixing member via the locking arm and a second position where the axial position of the second fixing member is fixed relative to the first fixing member via the locking arm, and wherein the locking arm is configured to pivot about the pivot mechanism to move between the first position and the second position.

2. The locking mechanism of claim 1, wherein the first fixing member is configured to be coupled to the introducer sheath, proximate to a patient point of entry at which the introducer sheath enters a vessel of a patient from outside of the patient.

3. The locking mechanism of claim 1, wherein in the second position the locking arm is rigidly coupled to each of the first fixing member and the second fixing member and the handle is locked at a fixed distance from the introducer sheath via the locking arm.

4. The locking mechanism of claim 1, wherein in the first position the locking arm is rigidly coupled to only one of the first fixing member and the second fixing member and the handle is not locked at a fixed distance from the introducer sheath via the locking arm.

5. The locking mechanism of claim 1, wherein the locking arm is removably coupled to one of the first fixing member and the second fixing member via a clamping mechanism attached to the one of the first fixing member and the second fixing member.

6. The locking mechanism of claim 5, wherein the clamping mechanism is configured to receive and rigidly couple to the first end of the locking arm in the second position.

7. The locking mechanism of claim 1, wherein the second fixing member is a ring configured to extend around the handle of the delivery apparatus.

8. The locking mechanism of claim 1, wherein the first fixing member is a ring configured to be removably coupled to and around a proximal portion of the introducer sheath.

9. A method, comprising:
advancing a portion of a transcatheter delivery apparatus through an introducer sheath inserted into a vessel of a patient and to a target implantation site for a prosthetic valve, wherein a distal end portion of an outer shaft of the delivery apparatus forms a capsule enclosing the prosthetic valve in a radially compressed state, wherein the outer shaft extends distally from a handle of the delivery apparatus, and wherein the introducer sheath includes a proximal portion arranged external to a point of entry into the vessel of the patient and a distal portion arranged internal to the point of entry;
after the distal end portion of the outer shaft of the delivery apparatus reaches the target implantation site and prior to retracting the capsule to uncover the prosthetic valve, locking an axial position of the handle of the delivery apparatus relative to the proximal portion of the introducer sheath via coupling a proximal portion of a locking arm of a locking mechanism to a ring member arranged around the handle of the delivery apparatus, wherein a distal portion of the locking arm is attached to the proximal portion of the introducer sheath, and wherein the handle is arranged external to the point of entry;
retracting the outer shaft including the capsule, to uncover the prosthetic valve; and unlocking the axial position of the handle relative to the proximal portion of the introducer sheath via pivoting the proximal portion of the locking arm away from the ring member around the handle, and wherein the locking arm remains coupled to the proximal portion of the introducer shaft when the proximal portion of the locking arm is unlocked from the handle.

10. The method of claim 9, further comprising actuating one or more actuator assemblies extending from the handle and coupled to the prosthetic valve in the radially compressed state to radially expand the prosthetic valve and implant the prosthetic valve at the target implantation site.

11. The method of claim 10, further comprising releasing the one or more actuator assemblies from the prosthetic heart valve.

12. The method of claim 9, wherein locking the axial position of the handle relative to the proximal portion of the introducer sheath includes maintaining the handle at a fixed axial distance from the proximal portion of the introducer sheath.

13. The method of claim 9, wherein locking the axial position of the handle relative to the proximal portion of the introducer sheath further comprises maintaining the prosthetic valve at a desired axial position at the target implantation site during retraction of the outer shaft to uncover the prosthetic valve.

14. The method of claim 9, wherein retracting the outer shaft includes rotating a knob on the handle that is operatively connected to a proximal end portion of the outer shaft.

15. An assembly, comprising:

an introducer sheath;

a delivery apparatus including a handle and an outer shaft extending distally from the handle, wherein the outer shaft is movable, in an axial direction arranged along a central longitudinal axis of the delivery apparatus, relative to the handle, and wherein the handle comprises a rotatable knob for translating the outer shaft to deploy an implant mounted on the delivery apparatus; and a locking mechanism, comprising:

a locking arm having a first end portion permanently coupled to a proximal portion of the introducer sheath and a second end portion configured to be removably coupled to the handle, wherein the locking arm is movable between an unlocked, first position where the second end portion is not rigidly coupled to the handle and the handle is able to move, in the axial direction, relative to the proximal portion of the introducer sheath and a locked, second position where the second end portion is rigidly coupled to the handle and the handle is maintained at a fixed distance, in the axial direction, from the proximal portion of the introducer sheath; and a first ring member arranged around and coupled to the handle, wherein the locking arm is pivotable away from the first ring member to move from the locked, second position to the unlocked, first position.

16. The assembly of claim 15, wherein the second end portion of the locking arm is configured to be removably coupled to the handle via a clamping mechanism of the locking mechanism, the clamping mechanism attached to the handle via the first ring member.

17. The assembly of claim 16, wherein the clamping mechanism is a screw-clamp comprising a central bore adapted to receive the second end portion of the locking arm and wherein in the locked, second position the screw-clamp is rigidly coupled to the second end portion of the locking arm within the central bore.

18. The assembly of claim 15, wherein the locking mechanism further comprises a second ring member arranged around and removably coupled to the proximal portion of the introducer sheath, and wherein the second ring member is permanently coupled to the first end portion of the locking arm via a pivot mechanism.

19. The assembly of claim 15, wherein the proximal portion of the introducer sheath is configured to be arranged proximate to a point of entry into a vessel of a patient into which the introducer sheath is inserted.

20. The assembly of claim 15, wherein the implant is a prosthetic valve, and wherein the delivery apparatus is adapted to carry the prosthetic valve in a radially compressed state within a distal end of the outer shaft.

* * * * *